(12) United States Patent
Paulsen et al.

(10) Patent No.: US 9,541,513 B2
(45) Date of Patent: Jan. 10, 2017

(54) METHOD FOR NUCLEAR MAGNETIC RESONANCE DIFFUSION MEASUREMENTS

(71) Applicant: SCHLUMBERGER TECHNOLOGY CORPORATION, Sugar Land, TX (US)

(72) Inventors: Jeffrey L. Paulsen, Brookline, MA (US); Yi-Qiao Song, Newton, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 707 days.

(21) Appl. No.: 13/958,820

(22) Filed: Aug. 5, 2013

(65) Prior Publication Data

US 2014/0184220 A1    Jul. 3, 2014

Related U.S. Application Data

(60) Provisional application No. 61/748,704, filed on Jan. 3, 2013.

(51) Int. Cl.
*G01N 24/08* (2006.01)
*G01R 33/44* (2006.01)
(Continued)

(52) U.S. Cl.
CPC ........... *G01N 24/081* (2013.01); *G01R 33/448* (2013.01); *G01R 33/56341* (2013.01); *G01V 3/32* (2013.01)

(58) Field of Classification Search
CPC . G01R 33/448; G01R 33/54; G01R 33/56341; G01N 24/081
See application file for complete search history.

(56) References Cited

U.S. PATENT DOCUMENTS 6,842,000 B2 *  1/2005  Norris ............. G01R 33/56509
                                                    324/309
7,541,809 B2 *  6/2009  Miyoshi ................. A61B 5/055
                                                    324/306
(Continued)

FOREIGN PATENT DOCUMENTS

WO        9209901 A1    6/1992
WO     2007087494 A2    8/2007

OTHER PUBLICATIONS

Blumler, et al., "Chapter 54: Review: NMR Detection and Characterization of Hydrocarbons in Subsurface Earth Formations", Spatially Resolved Magnetic Resonance: Methods, Materials, Medicine, Biology, Rheology, Geology, Ecology, Hardware, 2007, pp. 555-573.

(Continued)

*Primary Examiner* — Gregory H Curran
(74) *Attorney, Agent, or Firm* — John Vereb

(57) ABSTRACT

A method and system for determining a property of a substance using nuclear magnetic resonance (NMR) is described herein. The method includes applying a NMR pulse sequence to the substance. The NMR pulse sequence includes a first set of pulses and a second set of pulses. The first set of pulses and the second set of pulses encode for overlapping diffusion times. By overlapping diffusion times, the NMR pulse sequence can be used to measure a diffusion coefficient for a first diffusion time, a diffusion coefficient for a second diffusion time, and a correlation between the two overlapping diffusion times. This information, in turn, can be used to differentiate between intrinsic bulk diffusivity of the substance and the reduced diffusivity of the substance caused by restricted diffusion.

19 Claims, 16 Drawing Sheets

(51) Int. Cl.
    G01R 33/563    (2006.01)
    G01V 3/32      (2006.01)

(56) References Cited

U.S. PATENT DOCUMENTS

2004/0189296 A1   9/2004   Sun et al.
2005/0007100 A1   1/2005   Basser et al.
2010/0033182 A1   2/2010   Ozarslan et al.

OTHER PUBLICATIONS

Callaghan, et al., "Diffusion-diffusion correlation and exchange as a signature for local order and dynamics", Journal of Chemical Physics, vol. 120(8), 2004, pp. 4032-4038.

Chen, et al., "Quantitative NMR imaging of multiphase flow in porous media", Magnetic Resonance Imaging, vol. 10, No. 5, 1992, pp. 815-826.

Cheng, et al., "Multiple Scattering by NMR", Journal of the American Chemical Society, vol. 121, Aug. 14, 1999, pp. 7935-7936.

Hurlimann, et al., "Experimental Investigation of Split 180° Sequences", date unavailable, pp. 1-32.

Hurlimann, et al., "Hydrocarbon Composition From NMR Diffusion and Relaxation Data", Petrophysics, vol. 50, No. 2, 2009, pp. 116-129.

Jespersen, et al., "The displacement correlation tensor: Microstructure, ensemble anisotropy and curving fibers", Journal of Magnetic Resonance, vol. 208, Issue 1, Jan. 2011, pp. 34-43.

Jespersen, Sune Norhoj, "Equivalence of double and single wave vector diffusion contrast at low diffusion weighting", NMR in Biomedicine vol. 25, Issue 6, 2012, pp. 813-818.

Lawrenz, et al., "A tensor model and measures of microscopic anisotropy for double-wave-vector diffusion-weighting experiments with long mixing times", Journal of Magnetic Resonance, vol. 202, Issue 1, Jan. 2010, pp. 43-56.

Mitra, Partha P., "Multiple wave-vector extensions of the NMR pulsed-field-gradient spin-echo diffusion measurement", Physical Review B, vol. 51, Jun. 1, 1995, pp. 15074-15078.

Mitra, et al., "Short-Time Behavior of the Diffusion Coefficient as a Geometrical Probe of Porous Media", Physical Review B, vol. 47, No. 14, Apr. 1, 1993, pp. 8565-8574.

Ozarslan, et al., "Microscopic anisotropy revealed by NMR double pulsed field gradient experiments with arbitrary timing parameters", Journal of Chemical Physics, vol. 128, No. 15, 2008, pp. 154511-1 to 154511-11.

Price, William, "Pulsed-field gradient nuclear magnetic resonance as a tool for studying translational diffusion: Part II. Experimental Aspects", Concepts in Magnetic Resonance, vol. 10, Issue 4, Jun. 1998, pp. 197-237.

Song, Yi-Qiao, "Novel NMR techniques for porous media research", Cement and Concrete Research, vol. 37, Issue 3, Mar. 2007, pp. 325-328.

Zielinski, et al., "Combined effects of diffusion, nonuniform-gradient magnetic fields, and restriction on an arbitrary coherence pathway", Journal of Chemical Physics, vol. 119(2), 2003, pp. 1093-1104.

Callaghan, et al., "Velocity Exchange Spectroscopy", Journal of Magnetic Resonance, Series A, vol. 106, Issue 2, Feb. 1994, pp. 260-265.

Latour, et al., "Time-Dependent Diffusion Coefficient of Fluids in Porous Media as a Probe of Surface-to-Volume Ratio", Journal of Magnetic Resonance, Series A, vol. 101, Issue 3, Feb. 15, 1993, pp. 342-346.

\* cited by examiner

METHOD FOR NUCLEAR MAGNETIC RESONANCE DIFFUSION MEASUREMENTS

CROSS-REFERENCE TO RELATED APPLICATION

The present application claims the benefit of U.S. Provisional Patent Application Ser. No. 61/748,704 filed Jan. 3, 2013, which is incorporated herein by reference in its entirety.

TECHNICAL FIELD

This disclosure relates to nuclear magnetic resonance (NMR) and, in particular, NMR diffusion measurements.

BACKGROUND

Nuclear magnetic resonance (NMR) can be used to determine properties of a substance. An NMR method includes applying a static magnetic field to the substance. The static magnetic field generates an initial magnetization of atomic nuclei within the substance. Then, an oscillating magnetic field is applied at a particular frequency to the substance. The oscillating field is composed of a sequence of radio frequency (RF) pulses that tip the magnetization of the atomic nuclei away from the initial magnetization. The sequence of pulses can be arranged so that the pulses and the static field interact with the nuclei to produce a NMR signal composed of "echoes" within at least a portion of the substance. The NMR signal is detected and can be used to determine properties of the substance.

In the oil and gas field industry, NMR is used to investigate the properties of subterranean formations and fluids within the formations. The formation is a porous medium and the fluids (e.g., water, oil and/or gas) within formations are contained within pore volumes of the formation. At least three different NMR measurements can be used to determine properties of a porous medium and a fluid contained therein: (i) a measurement of the absolute signal intensity of the NMR signal, (ii) a measurement of NMR signal relaxation and (iii) a measurement of diffusion. The relaxation measurement measures an inherent signal decay produced by atomic nuclei, whereas a diffusion measurement measures an additional decay produced by movement of the atomic nuclei. The absolute signal intensity can be used to determine the porosity of the porous medium. The relaxation measurement and diffusion measurement can be used to determine the pore size distribution of the porous medium and fluid type contained within the porous medium. For example, estimates of bound water, oil composition, and oil viscosity can be determined using relaxation measurements and diffusion measurements.

In particular, diffusion measurements are used to determine a diffusion coefficient of a fluid, which characterizes the distance that nuclei within the fluid will travel as a function of time. In an open or large volume, the diffusion coefficient of the fluid is known as a bulk diffusion coefficient. When the pore size within the formation is large, the measured diffusion coefficient will be similar to the bulk diffusion coefficient. However, in many cases, the pore size is small and this small pore size reduces the measured diffusion coefficient by impeding the movement of the nuclei within the fluid. Diffusion that is impeded by small pore size is known as restricted diffusion.

Diffusion measurements and relaxation measurements will both depend on the mobility of nuclei in a large bulk volume and the impediment caused by collisions with pore surfaces. For example, a fluid with high viscosity will have a smaller diffusion coefficient and a shorter relaxation time. Similarly, a porous medium with a small pore size will also shorten the diffusion coefficient and the relaxation time for a fluid. As explained above, however, diffusion and relaxation are affected by different mechanisms. Relaxation time is based on the inherent signal decay produced by atomic nuclei, whereas the diffusion coefficient is based on movement of atomic nuclei. So while these measurements are often correlated, each measurement can yield unique information. For instance, bound water will have a shortened $T_2$ relaxation time distribution. This shortened $T_2$ relaxation time distribution may intersect the $T_2$ relaxation time distribution of viscous oil in a large pore. However, an apparent diffusion coefficient (e.g., measured diffusion coefficient) of oil will still be orders of magnitude smaller than the apparent diffusion coefficient for water.

Nonetheless, diffusion measurements can be complicated when pore sizes are small and when two or more different fluids are located within pore volumes of a porous medium. Past diffusion measurement techniques yield limited or ambiguous information, especially in complex samples (e.g., porous media with different types of fluid). When characterizing oil composition, especially in emulsions or tight oil wet pores, differentiating the effects of composition and pore size is greatly complicated because bulk oil intrinsically has a broadened distribution of diffusion and relaxation times due to its varied composition. For such reasons, past diffusion and relaxation measurement techniques cannot unambiguously differentiate between restricted diffusion and composition of the fluid.

One technique used in magnetic resonance imaging (MRI) to make diffusion measurements of fluids within porous medium is known as a pulsed field gradient (PFG). A PFG is a short, timed pulse with spatially dependent magnetic field intensity. A PFG method applies pulses of magnetic field gradients along multiple directions along with a corresponding NMR pulse sequence (with RF pulses) to achieve spatial resolution (e.g., often referred to as "encoding"). The PFG can be used to detect molecular diffusion in fluids and obtain diffusion coefficients. A PFG sequence includes a pair of PFG pulses of identical amplitude (g) and duration ($\delta$). These two PFG pulses are separated by a time period ($\Delta$) (referred to as diffusion time). FIG. 1 shows a prior art PFG pulse sequence 100 that can be applied to a fluid within a porous medium (e.g., a sample). The sequence 100 includes an excitation pulse 102 (e.g., single 90-degree RF pulse) to rotate the spin magnetization of the nuclei within the fluid to the transverse plane. The excitation pulse 102 excites the spins of the nuclei for encoding and detection. A first gradient pulse 104 encodes the initial position of the nuclei as a phase imprinting a wave of magnetization across the fluid. Afterwards, the nuclei move due to diffusion over a diffusion time ($\Delta$), while retaining the initial encoded phase. A second gradient pulse 106 of negative amplitude re-encodes for the position of the nuclei, but with opposite phase such that the net signal phase of each nuclei is proportional to its displacement.

The pulse sequence can be modified to improve its application for various different samples. For example, FIG. 2 shows another prior art PFG pulse sequence 200. The sequence 200 shown in FIG. 2 uses a spin echo RF sequence that has an excitation pulse 202 (a 90-degree pulse) for excitation and a refocusing pulse 204 (a 180-degree pulse) for refocusing to generate an echo. Because of the use of the refocusing pulse, the corresponding gradient pulses 206 and 208 are of the same sign (either positive or negative). The pulse sequences shown in FIGS. 1 and 2 are often referred to as single-pulse field gradient (or s-PFG).

Each PFG pulse is defined by an area parameter (q), which is further defined in units of reciprocal distance (e.g., mm$^{-1}$). This reciprocal distance corresponds to a wavelength of a wave vector imprinted across the sample by the first pulse and refocused by the second pulse. The area parameter (q) can be determined according to the following relationship:

$$q=\gamma g\delta, \quad (1)$$

where $\gamma$ is the gyromagnetic ratio of the nuclei (s$^{-1}$ G$^{-1}$), g is the amplitude of the gradient pulse (G/cm), and $\delta$ is the width (or duration) of the pulse (s).

The NMR signal that is generated by the PFG pulses exhibits a decay. This decay is represented by the following relationship:

$$E(q)=E(0)\exp(-D\Delta q^2), \quad (2)$$

where D is the diffusion coefficient of the fluid, $\Delta$ is the diffusion time, and E is NMR signal data obtained from the generated NMR signal (e.g., signal amplitude). According to equation 2, encoding for diffusion is characterized by the area parameter of the gradient pulses (q). To obtain a diffusion coefficient, a series of experiments with different values of area parameters (q) or diffusion times ($\Delta$) can be performed and the NMR signal data obtained from the experiments (E) is analyzed using equation 2 above.

FIG. 3 shows another example of a prior art pulse sequence 300 that can be applied to a fluid within a porous medium. This pulse sequence 300 is often referred to as a double-pulsed-field-gradient (d-PFG). The d-PFG pulse sequence 300 includes an initial excitation pulse 302 that excites the spins of the nuclei within the fluid. The sequence 300 also includes two pairs of gradient pulses 304 ($q_1$) and 306 ($q_2$) that are separated by a mixing time ($T_m$). Each pair of gradient pulses 304, 306 encode for displacement by imprinting and refocusing a wave-vector spatially across the sample, after which the NMR signal produced by the sequence is acquired. The d-PFG pulse sequence 300 uses two diffusion periods ($\Delta_1$) and ($\Delta_2$) to obtain correlation of the diffusive displacement during and between these two diffusion times. The d-PFG pulse sequences are applied a number of times while the area parameters ($q_1$) and ($q_2$) are held constant and a gradient angle ($\theta$) between the pairs of gradient pulses is varied. In various embodiments, the first pair 304 is applied along a single direction (e.g., x-axis) and the second pair 306 is applied along a different direction (e.g., y axis). As the d-PFG pulse sequences are applied, the second direction is varied and the gradient angle ($\theta$) between the pairs thus also varies. A plot of the NMR signal for different values of the gradient angle ($\theta$) can potentially show modulation due to time dependent diffusion and diffusion anisotropy. Although such d-PFG pulse sequences can potentially identify anisotropically shaped pores when the pores are distributed isotropically in a bulk porous medium, such d-PFG techniques are less effective for heterogeneous porous media.

In another example, the d-PFG pulse sequence can be applied to a fluid within a heterogeneous porous medium a number of times using a variable mixing time ($T_m$) between the two diffusion periods ($\Delta_1$) and ($\Delta_2$) to assess connectively between different regions in the medium. The d-PFG pulse sequence 300 can be used to correlate diffusion over the first diffusion period ($\Delta_1$) versus the second diffusion period ($\Delta_2$). A two-dimensional Laplace inversion can be used to analyze the obtained NMR signal data (E) using the following relationship:

$$E(q_1,q_2)=E(0,0)\exp(-D_1\Delta q_1^2-D_2\Delta q_2^2) \quad (3)$$

where $D_1$ is the diffusion coefficient during the first diffusion period ($\Delta_1$) and $D_2$ is the diffusion coefficient during the second diffusion period ($\Delta_2$). This method of varying mixing times ($T_m$) does not measure or consider the time-dependent diffusion in porous media. The method uses a very long mixing times ($T_m$) to obtain a valid result, which in turn is problematic because the signal produced by the initial pair of gradient pulses decays over long mixing times. When a d-PFG pulse sequence 300 is used with a short mixing time ($T_m$), there is not sufficient movement of nuclei between the two different regions of the porous media. Thus, when the mixing time ($T_m$) is short, the diffusion coefficient during the first diffusion period ($\Delta_1$) and the diffusion coefficient during the second diffusion period ($\Delta_2$) are approximately equal.

For the reasons stated above, past diffusion measurements have difficulty effectively and efficiently differentiating between intrinsic bulk diffusivity of a fluid within a porous medium and the reduced diffusivity of the fluid caused by restricted diffusion.

SUMMARY

Illustrative embodiments of the present disclosure are directed to a method for determining a property of a substance using nuclear magnetic resonance (NMR). The method includes applying a NMR pulse sequence to the substance. The NMR pulse sequence includes a first set of pulses and a second set of pulses that encode for overlapping diffusion times. A NMR signal produced by the NMR pulse sequence is detected to obtain NMR signal data. The property of the substance can be determined using the NMR signal data over each of the overlapping diffusion times. By overlapping diffusion times, the NMR pulse sequence can be used to measure a diffusion coefficient for a first diffusion time, a diffusion coefficient for a second diffusion time and a correlation between the overlapping diffusion times. This information, in turn, can be used to differentiate between intrinsic bulk diffusivity of the substance and the reduced diffusivity of the substance caused by restricted diffusion.

In another more specific embodiment, the first set of pulses includes two pulses that are each defined by a first area parameter and separated by a time period. Similarly, the second set of pulses includes two pulses that are each defined by a second area parameter and separated by the time period. The NMR pulse sequence is applied a number of times and each application of the NMR pulse sequence uses different values for the first area parameter and/or the second area parameter. The method further includes detecting NMR signals produced by each application of the NMR pulse sequence to obtain NMR signal data. A Laplace inversion is performed on the NMR signal data to obtain diffusion coefficients for the first diffusion time and the second diffusion time. A property of the substance can be determined using these diffusion coefficients, such as a bulk diffusion coefficient of the substance.

In a further specific embodiment, the first set of pulses and the second set of pulses include a portion of pulses that correspond to the first diffusion time and a complimentary portion of pulses that correspond to the second diffusion time. The values of the first area parameter and the second area parameter are varied according to the following relationships:

$$q_s=q_1+q_2,$$

$$q_d=q_2-q_1,$$

where $q_1$ is the first area parameter, $q_2$ is the second area parameter, $q_s$ is an area parameter for the portion of pulses that correspond to the first diffusion time, and $q_d$ is an area parameter for the complimentary portion of pulses that correspond to the second diffusion time.

Illustrative embodiments are also directed to a system for determining a property of a substance. The system includes an NMR system for applying NMR pulse sequences to a substance and detecting NMR signals generated by the substance to obtain NMR signal data. The system further includes a processor and a memory storing instructions executable by the processor to perform processes. Those processes include providing an NMR pulse sequence to the NMR system. The NMR pulse sequence includes a first set of pulses and a second set of pulses that encode for overlapping diffusion times. Furthermore, the processes include determining the property of the substance using the NMR signal data over each of the overlapping encoding times.

BRIEF DESCRIPTION OF THE DRAWINGS

Those skilled in the art should more fully appreciate advantages of various embodiments of the disclosure from the following "Description of Illustrative Embodiments," discussed with reference to the drawings summarized immediately below.

DESCRIPTION OF ILLUSTRATIVE EMBODIMENTS

Illustrative embodiments of the present disclosure are directed to a method and system for determining a property of a substance using nuclear magnetic resonance (NMR). The method includes applying a NMR pulse sequence comprising a first set of pulses and a second set of pulses to the substance. The first set of pulses and the second set of pulses encode for a first diffusion time and a second diffusion time. These diffusion times overlap. By overlapping diffusion times, the NMR pulse sequence can be used to measure a diffusion coefficient for the first diffusion time, a diffusion coefficient for the second diffusion time, and a correlation between the overlapping diffusion times. This information, in turn, can be used to differentiate between intrinsic bulk diffusivity of the substance and the reduced diffusivity of the substance caused by restricted diffusion. Details of various embodiments are discussed below.

Figure 1:
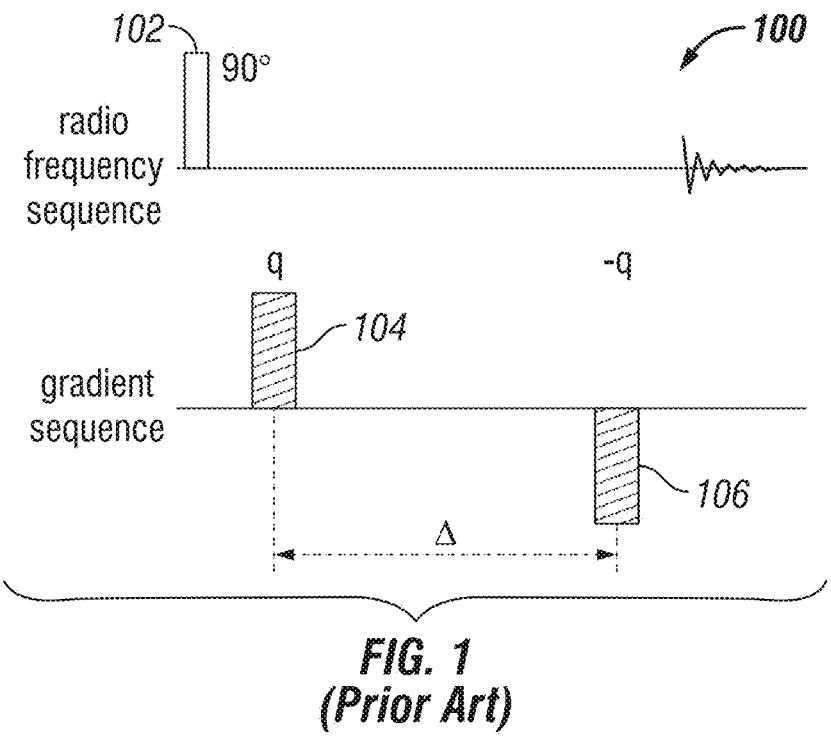
FIG. 1 shows a prior art pulsed field gradient (PFG) sequence.
Figure 2:
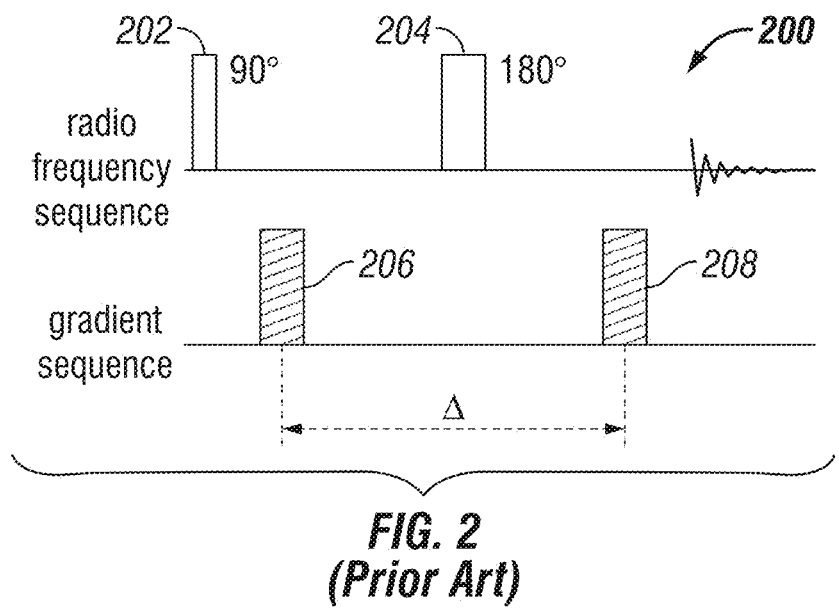
FIG. 2 shows another prior art PFG sequence.
Figure 3:
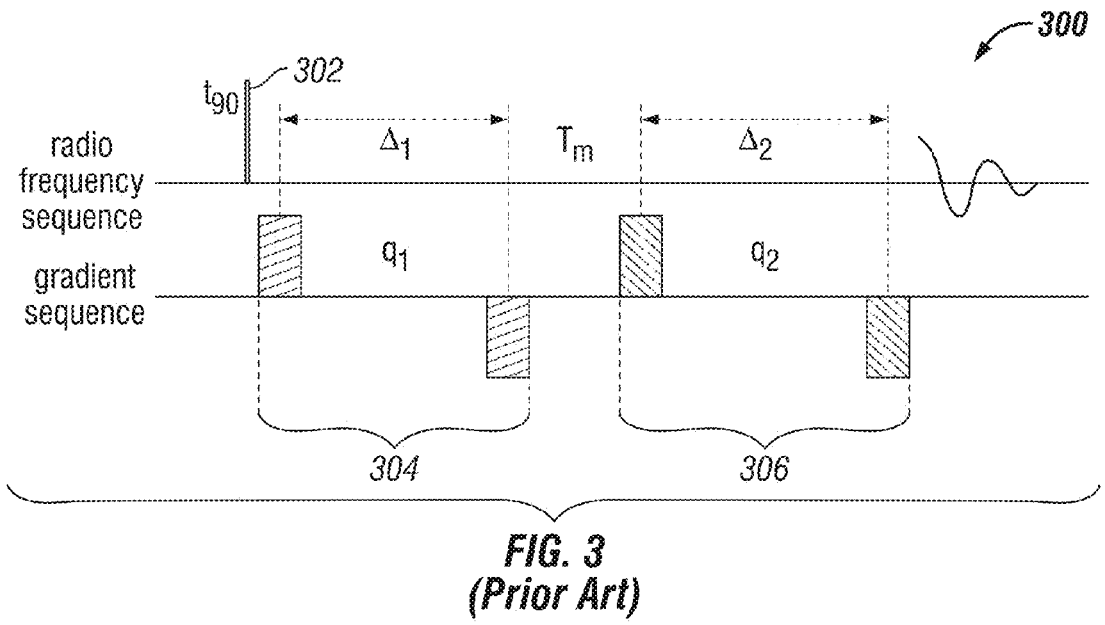
FIG. 3 shows a prior art double-pulsed-field-gradient (d-PFG) sequence.
Figure 4:
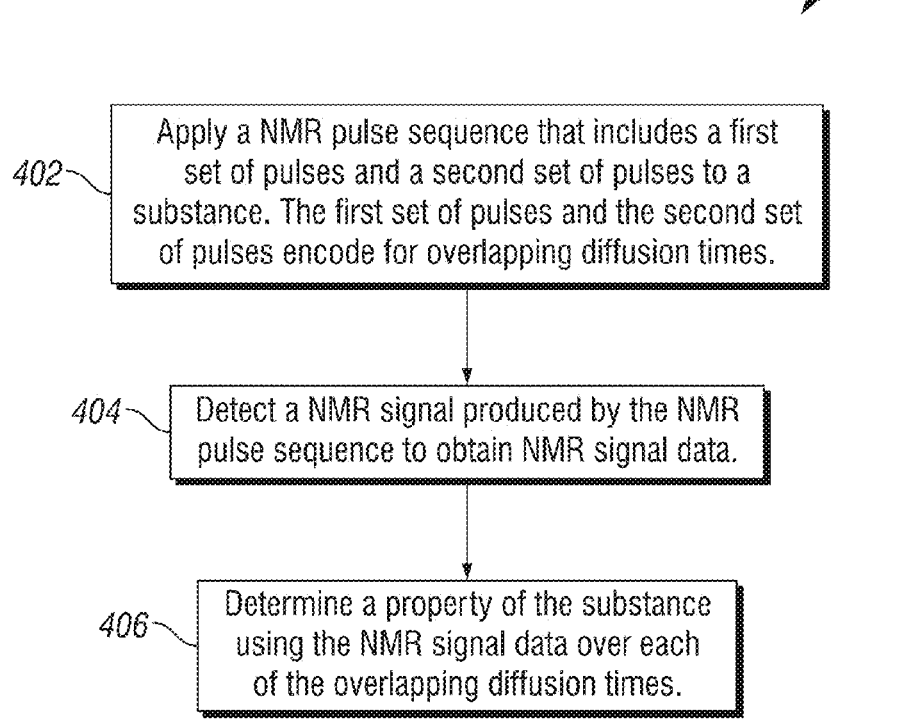
FIG. 4 shows a method for determining a property of a substance in accordance with one embodiment of the present disclosure.
Figure 5:
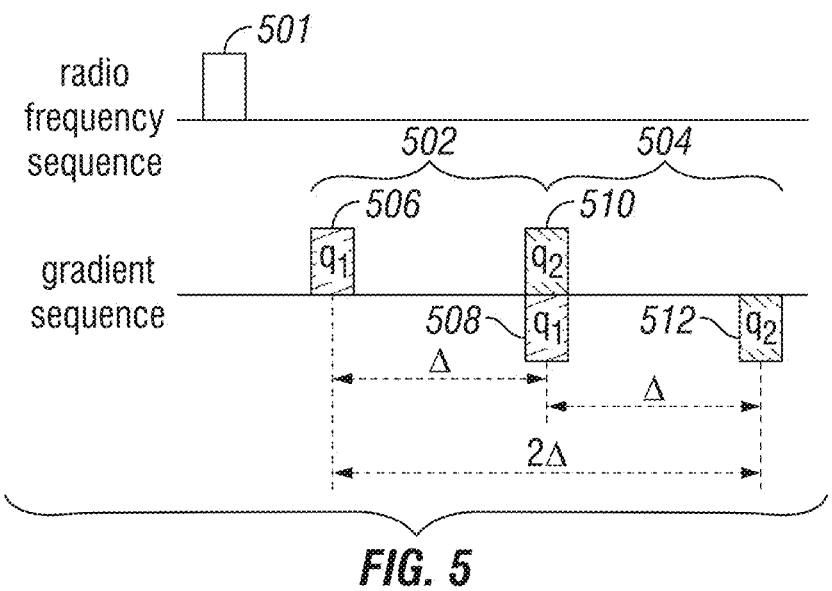
FIG. 5 shows a nuclear magnetic resonance (NMR) pulse sequence in accordance with one embodiment of the present disclosure.

FIG. 4 shows a method 400 for determining a property of a substance using NMR. Before the first process 402, a sample, such as a rock core, is placed in an NMR system, such as an NMR rock core analyzer. Process 402 includes using the NMR system to apply a NMR pulse sequence to the substance. FIG. 5 shows one example of an NMR pulse sequence 500 that is applied to the substance. The NMR pulse sequence 500 includes a radio frequency excitation pulse 501 followed by at least a first set of pulses 502 and a second set of pulses 504. The first set of pulses 502 and the second set of pulses 504 are gradient pulses that generate a pulsed field gradient. A pulsed field gradient is a short, timed pulse with spatially dependent magnetic field intensity. In other embodiments, the first set of pulses 502 and the second set of pulses 504 are radio frequency pulses that are used to generate an "effective" pulsed field gradient, as further described below with respect to FIGS. 17 and 18. The sets of pulses may include one or more pulses. In this case, the first set of pulses 502 includes a first pulse 506 and a second pulse 508 that are each defined by a first area parameter ($q_1$) and separated by a time period (Δ). The second set of pulses 504 includes a first pulse 510 and a second pulse 512 that are each defined by a second area parameter ($q_2$) and separated by the time period (Δ). The area parameters are defined in units of reciprocal distance (e.g., $mm^{-1}$) and are defined by a pulse width (δ) and a pulse height (g), as shown in equation 1. The first pulse 506, 510 and the second pulse 508, 512 within each set include area parameters that cancel. To this end, in some embodiments, the pulses have opposite amplitudes, as shown in FIG. 5.

The first set of pulses 502 and the second set of pulses 504 encode for overlapping diffusion times. In this case, the first set of pulses 502 and the second set of pulses 504 encode for a first diffusion time (2Δ) and a second diffusion time (Δ). As shown in FIG. 5, the diffusion times overlap because at least part of the second diffusion time (Δ) is within the boundaries of the first diffusion time (2Δ). The first set of pulses 502 and the second set of pulses 504 are applied consecutively to generate the overlapping diffusion times. More specifically, to generate the overlapping diffusion times, the first pulse 510 of the second set of pulses 504 is applied (i) simultaneously with the last pulse 508 of the first set 502, (ii) as soon as the last pulse ends, or (iii) a short time period after the last pulse ends. The short time period is short enough so that the magnetizations produced by each of the first set of pulses 502 ($q_1$) and the second set of pulses 504 ($q_2$) interact with each other to form overlapping diffusion periods. Furthermore, this short time period is short enough so that negligible diffusive motion occurs during the short time period relative to the diffusion times Δ and 2Δ. The short time period will be less than a shortest encoded diffusion time (e.g., the second diffusion time (Δ)) and, in various embodiments, will be less than five times the pulse width (δ) of the pulses within the two sets to optimally preserve the overlapping diffusion times.

In some embodiments, the NMR pulse sequence 500 may include more than two sets of pulses that encode for more than two diffusion times.

Figure 6:
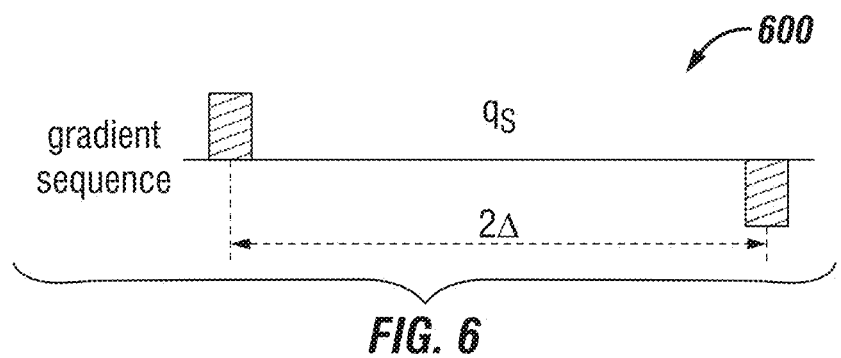
FIG. 6 shows a portion of pulses from the sequence in FIG. 5 that encode for a first diffusion time (2Δ) in accordance with one embodiment of the present disclosure.
Figure 7:
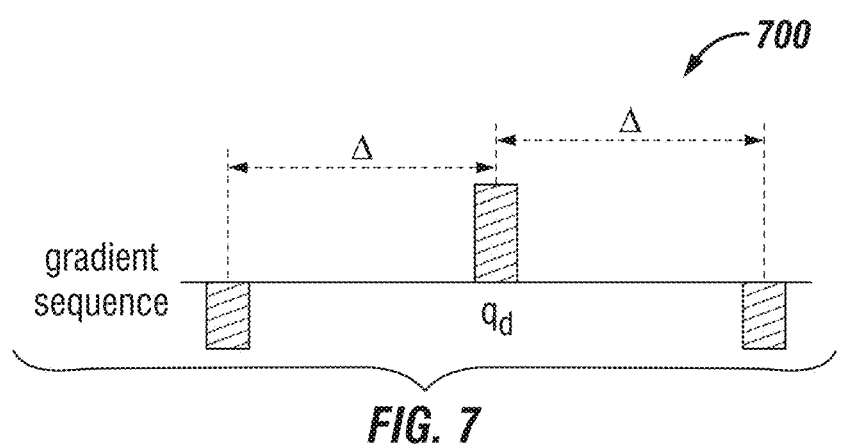
FIG. 7 shows a complimentary portion of pulses from the sequence in FIG. 5 that encode for a second diffusion time (Δ) in accordance with one embodiment of the present disclosure.

The first set of pulses 502 and the second set of pulses 504 include a portion of pulses that correspond to the first diffusion time (2Δ) and a complimentary portion of pulses that correspond to the second diffusion time (Δ). FIG. 6 shows the portion of pulses 600 that are responsible for encoding the first diffusion time (2Δ). This portion of pulses 600 has an area parameter ($q_s$). FIG. 7 shows the complimentary portion of pulses 700 that is responsible for encoding the first diffusion time (2Δ) and also the second diffusion time (Δ). The complimentary portion of pulses 700 has an area parameter ($q_d$). The pulses 600, 700 shown in FIGS. 6 and 7 are portions of the first and second sets of pulses 502 ($q_1$) and 504 ($q_2$) in anti-symmetric ($q_s$) and symmetric ($q_d$) gradient waveforms. The area parameters for the portions 600, 700 are defined according to the following relationships:

$$q_s = q_1 + q_2, \quad (4)$$

$$q_d = q_2 - q_1, \quad (5)$$

where $q_1$ is the first area parameter, $q_2$ is the second area parameter, $q_s$ is the area parameter for the portion of pulses 600 that correspond to the first diffusion time (2Δ), and $q_d$ is the area parameter for the complimentary portion of pulses 700 that correspond to the second diffusion time (Δ).

Figure 8:
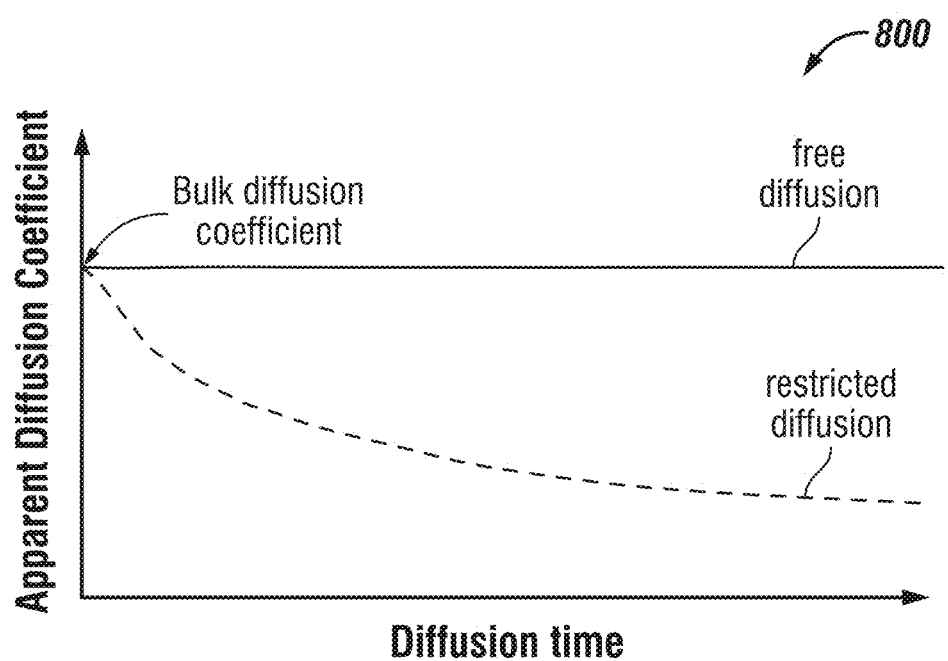
FIG. 8 shows a plot of diffusion coefficients versus diffusion time.

FIG. 8 shows a plot 800 for a diffusion coefficient versus diffusion time. As shown in the plot 800, when nuclei experience free diffusion (e.g., in an open environment), the diffusion coefficient is independent of the diffusion time and equivalent to the bulk diffusion coefficient. When nuclei experience restricted diffusion (e.g., in a porous medium), the diffusion coefficient varies with diffusion time. By encoding for two different diffusion times, the pulse sequences described herein can differentiate between restricted diffusion and bulk diffusion.

Figure 9:
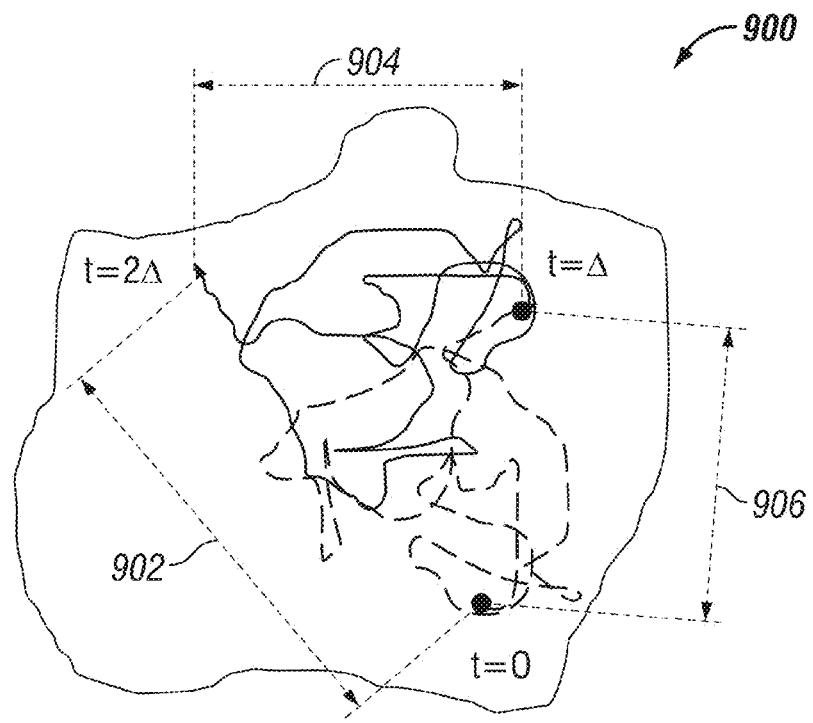
FIG. 9 shows a diffusion path for a nucleus over two different diffusion times that overlap in accordance with one embodiment of the present disclosure.
Figure 10:
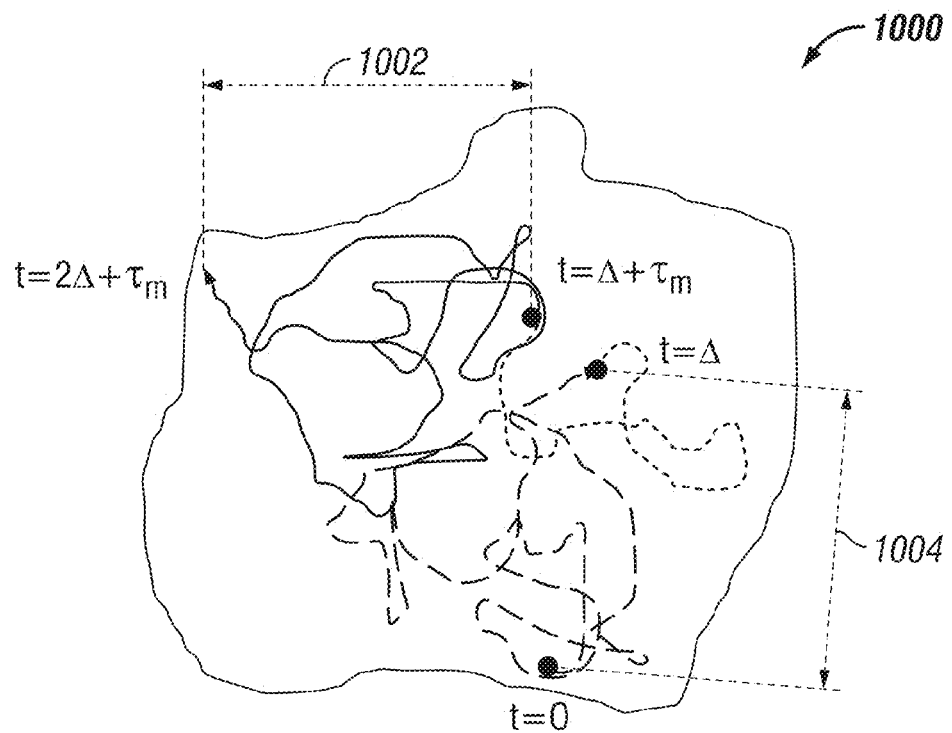
FIG. 10 shows a diffusion path for a nucleus over different diffusion times that do not overlap.

FIG. 9 shows a diffusion path 900 for a nucleus over two different diffusion times that overlap. Specifically, FIG. 9 shows how the portion of pulses ($q_s$) and complimentary portion of pulses ($q_d$) are sensitive to the movement of the nucleus over two different diffusion times. As shown in FIG. 9, the portion ($q_s$) is sensitive to displacement in directions 902 over the first diffusion time 2Δ. The complimentary portion of pulses ($q_d$) is sensitive to three displacements 902, 904 and 906 over the second diffusion time period (Δ). Because the portion ($q_s$) and the complimentary portion ($q_d$) are applied over overlapping diffusion times, the portions encode for the movement of the nucleus simultaneously and encode for diffusion over both the first diffusion time (2Δ) and the second diffusion time (Δ). Thus, an observation of diffusion over the second diffusion time period (Δ) can be correlated to its corresponding values for diffusion over the first time period (2Δ). In contrast, FIG. 10 shows a diffusion path 1000 over a first diffusion time and a second diffusion time that do not overlap (e.g., in the case of past d-PFG pulse sequences). In particular, FIG. 10 shows how a first set of pulses ($q_1$) and second set of pulses ($q_2$) are sensitive to the movement of the nucleus. The first set of pulses ($q_1$) is sensitive to displacement 1002 of the nucleus during the first diffusion time ($Δ_1$) and the second set of pulses ($q_2$) is sensitive to displacement in direction 1004 during the second diffusion time period ($Δ_2$). In this case, the diffusion times do not overlap and thus the pulse sequences are not sensitive to total displacement 902, as shown in FIG. 9. In the case of past d-PFG pulse sequences, when the first diffusion time ($Δ_1$) is equal to the second diffusion time ($Δ_2$), the pulse sequence and corresponding measurement are sensitive to diffusion over one time and, thus, cannot differentiate restricted diffusion from a reduction in the diffusion coefficient due to encoding time. When the first diffusion time ($Δ_1$) is different from the second diffusion time ($Δ_2$), the pulse sequence and corresponding measurement measure diffusion over two diffusion times, but the corresponding measurement cannot differentiate between restricted diffusion and nuclei exchange between two different environments, such as movement between two pores of different sizes. This is because displacements 1002 and 1004 are disjointed and may traverse two different environments. In contrast, the overlapping diffusion periods correspond to total displacement 902 using $q_s$ and its subdivisions 904, 906 using $q_d$.

Figure 11:
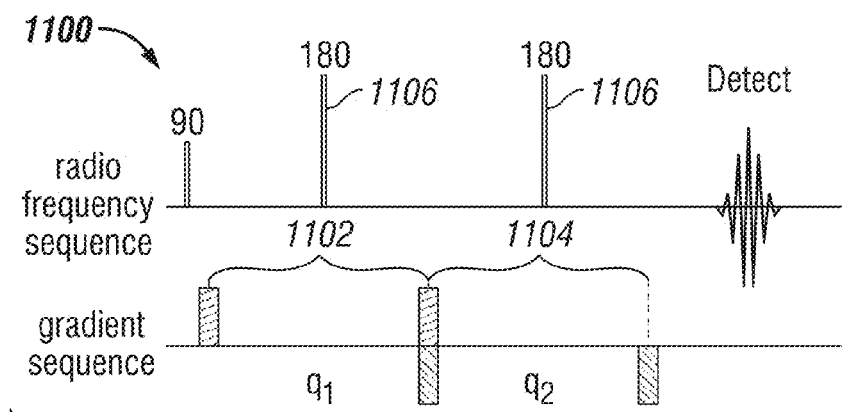
FIG. 11 shows a pulse sequence with refocusing pulses in accordance with one embodiment of the present disclosure.

Illustrative embodiments of the present disclosure are not limited to the pulse sequence shown in FIG. 5. Other pulse sequences and additional pulse sequences can also be used to encode overlapping diffusion times. For example, FIG. 11 shows a pulse sequence 1100 with two sets of gradient pulses 1102, 1104 and refocusing pulses 1106 that minimize effects of background gradients. The refocusing pulses 1106 are 180 degree pulses that reverse the phase of spins produced by an excitation pulse and compensate for a range of different resonant NMR frequencies due to, for example, the use of an imperfect magnet. In various embodiments, the amplitudes of some of the gradient pulses are flipped to account for the effect of the RF pulses on the gradient encoding. For example, a 180 refocusing pulse will change the encoding done by a prior gradient pulse as if the gradient pulse were originally applied with the opposite sign. Thus, any subsequent gradient pulses account for that effective sign of the gradient pulse.

Figure 12:
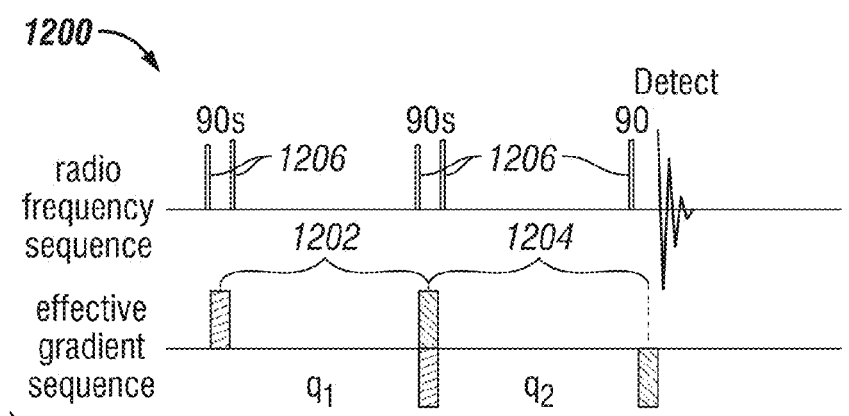
FIG. 12 shows a stimulated echo pulse sequence in accordance with one embodiment of the present disclosure.

FIG. 12 shows a stimulated echo pulse sequence 1200 with two sets of gradient pulses 1202, 1204. 90-degree pulses 1206 store and re-excite spins from their longitudinal axes during encoding times. This pulse sequence minimizes signal decay and is generally used to increase the range of practical encoding times.

Figure 13:
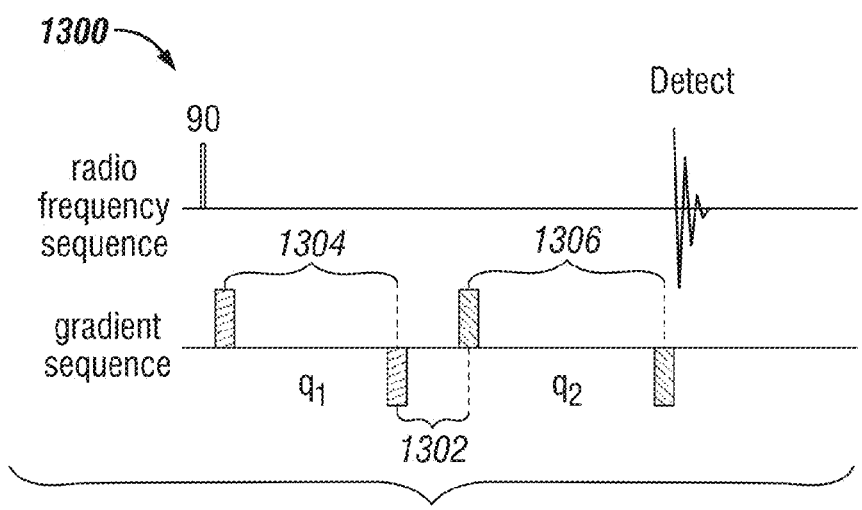
FIG. 13 shows a pulse sequence with a short time period between the two sets of pulses in accordance with one embodiment of the present disclosure.

FIG. 13 shows a pulse sequence 1300 with a short time period 1302 between the two sets of pulses 1302, 1306. In this embodiment, a short time period 1302 is included after the last pulse of the first set 1304 and before the first pulse of the second set 1306 (e.g., less than 50% of $\Delta$). As explained above, the short time period 1302 will be less than $\Delta$ and, in various embodiments, will be no more than five times the pulse width ($\delta$) to optimally preserve the overlapping encoding. When there is no time period between the two sets of pulses 1304, 1306, $q_s$ and $q_d$ are independent. Longer time periods between the two sets of pulses will produce a dependency between $q_s$ and $q_d$.

Figure 14:
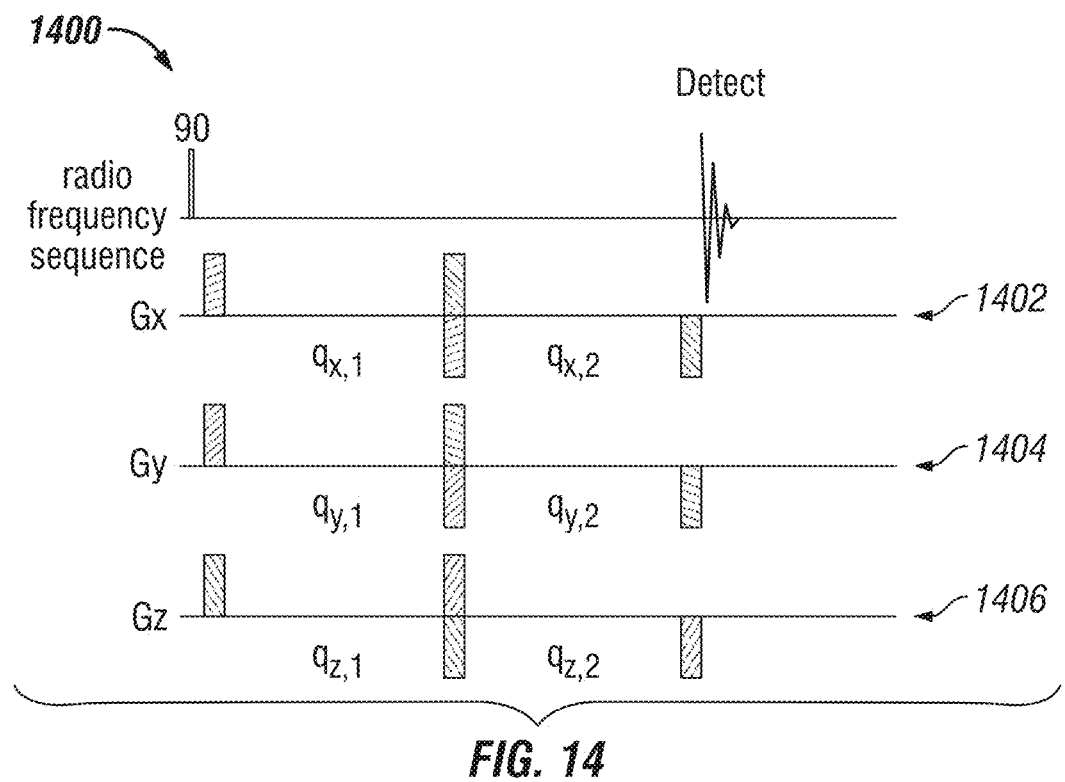
FIG. 14 shows a pulse sequence with multiple gradient axes pulses in accordance with one embodiment of the present disclosure.

FIG. 14 shows a pulse sequence 1400 with multiple gradient axes pulses. Often pulse field gradient encoding is done with gradients along different spatial axes. In this case, the pulse sequence 1400 includes an excitation pulse followed by two sets of gradient pulses in the x-direction 1402, y-direction 1404 and z-direction 1406.

Figure 15:
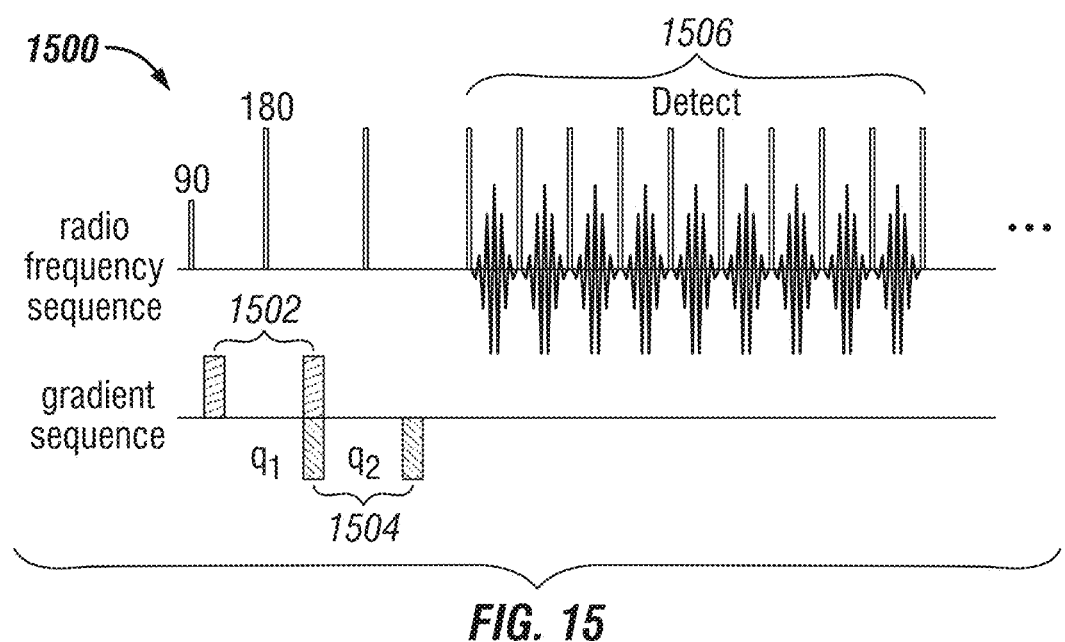
FIG. 15 shows a pulse sequence with a Carr Purcell Meiboom Gill (CPMG) encoding in accordance with one embodiment of the present disclosure.

FIG. 15 shows a pulse sequence 1500 with an additional encoding. The two sets of gradient pulses described herein can precede or follow any other type of NMR encoding (e.g., relaxation encoding, or imaging encoding). In this example, the two sets of gradient pulses 1502, 1504 are followed by a Carr Purcell Meiboom Gill (CPMG) acquisition 1506 to encode for $T_2$ relaxation.

Referring back to FIG. 4, at process 404, a NMR signal produced by the NMR pulse sequence within the substance is detected to obtain NMR signal data over the first and second diffusion time periods. In some embodiments, at process 406, the method ends when the NMR signal data over each of the overlapping diffusion times is then used to determine a diffusion coefficient of the substance. For example, if the diffusion coefficient at the first diffusion time (2$\Delta$) is equal to the diffusion time at the second diffusion time ($\Delta$), then the measured diffusion coefficient can be assumed to be the bulk diffusion coefficient.

In various other embodiments, processes 402 and 404 are repeated so that the NMR pulse sequence is applied to the substance a plurality of times using different values of area parameters for the portion of pulses ($q_s$) and the complimentary portion of pulses ($q_d$). The area parameters for the portions ($q_s$) and ($q_d$) can be varied by modifying the area parameters for the first and second sets of pulses ($q_1$) and ($q_2$) according to the relationships in equations 4 and 5. After each pulse sequence is applied, the generated NMR signal is detected to obtain an array of NMR signal data ordered according to $q_s$ and $q_d$ coordinates. In other embodiments, however, the area parameters for the first and second sets of pulses ($q_1$) and ($q_2$) are not varied according to the relationships in equations 4 and 5. Instead, each of the area parameters for the first and second sets of pulses ($q_1$) and ($q_2$) is varied to obtain an array of NMR signal data ordered according to, for example, $q_1$ and $q_2$ coordinates At process 406, the NMR signal data obtained from the repetitive application of the NMR pulse sequence to the substance is then used to determine a property of the substance. In particular, NMR signal data over each of the overlapping diffusion times is used to determine the property of the substance. The NMR signal produced by the NMR pulse sequence can be approximated by the following relationship:

$$\text{Ln } [E(q_1,q_2)]=-\Delta[q_1{}^2D(\Delta)+q_2{}^2D(\Delta)+2q_1(D(2\Delta)-D(\Delta))q_2] \quad (6)$$

Equation 6 was derived by using an approximation of a d-PFG signal, such as the approximation described in Sune Norhoj Jespersen, Equivalence of Double and Single Wave Diffusion Contrast at Low Diffusion Weighting, NMR in Biomedicine (Dec. 2, 2011). The approximation also assumed zero mixing time ($T_m$=0) and identical encoding times ($\Delta=\Delta_1=\Delta_2$). Accordingly, the generated NMR signal reflects the time dependence of diffusion over the times $\Delta$ and 2$\Delta$. Using the variables established in equations 4 and 5, the signal equation above for d-PFG with zero mixing time can be written as the following relationship:

$$E(q_s, q_d) = \exp\left\{-\frac{1}{2}\Delta[q_s^2 D(2\Delta) + q_d^2(2D(\Delta) - D(2\Delta))]\right\} \quad (7)$$

In the framework of $q_s$ and $q_d$, the contribution from $q_s$ and $q_d$ are separated and there are no cross-terms between $q_s$ and $q_d$. The two terms independently encode for diffusion over different and overlapping times—D(2$\Delta$) for $q_s$ and 2D($\Delta$)−D(2$\Delta$) for $q_d$. "D(2$\Delta$)" and "2D($\Delta$)−D(2$\Delta$)" are referred to herein as $D_s$ and $D_d$, respectively. In various embodiments, the second diffusion coefficient $D_d$ can be approximated as D($\Delta$). The relationship disclosed in equation 7 can be used to analyze NMR signal data in order to determine a property of the substance, such as presence of restricted diffusion, by observing a difference in D(2$\Delta$) and D($\Delta$) in the fit of equations 7 to the NMR signal data. In additional or other embodiments, a Laplace inversion is applied to the NMR signal data, as described below. The relationship defined by Equation 7 is different from the relationship defined by equation 6. The relationship defined by equation 6 exhibits a direct cross-term between $q_1$ and $q_2$. As a result, the relationship in equation 2 produces an incorrect result when the mixing time ($T_m$) of the d-PFG pulse is short. The new approach defined by equation 7 takes into consideration the relationship due to time-dependent diffusion and removes the cross-term.

For substances that contain a range of diffusion coefficients due to material mixture or pore size distribution, the relationship below can be used to approximate the NMR signal:

$$E(q_s, q_d) = \int dDf(D_s, D_d)\exp\left\{-\frac{1}{2}\Delta(q_s^2 D_s + q_d^2 D_d)\right\} \quad (8)$$

where $f(D_s, D_d)$ is a distribution function for diffusion coefficients that correspond to the number of nuclei whose diffusion coefficients at $\Delta$ and 2$\Delta$ correspond to ($D_s$, $D_d$). Equation 8 was derived by taking the integral of equation 7 over the distribution of diffusion coefficients. Accordingly, the NMR signal data obtained for independently selected values of $q_s$ and $q_d$ can be analyzed using equations 7 and 8 to obtain a two-dimensional plot of diffusion at the first diffusion time ($D_s$) versus diffusion at the second diffusion time ($D_d$).

Figure 16:
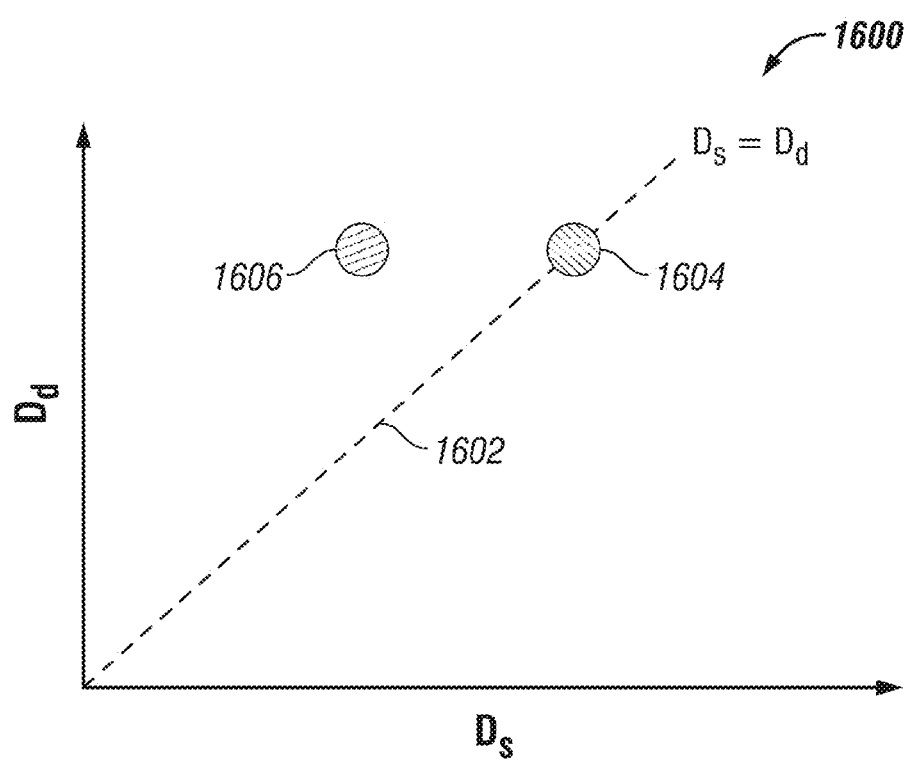
FIG. 16 shows a two-dimensional plot of diffusion coefficients at a first diffusion time ($D_S$) versus diffusion coefficients at the second diffusion time ($D_D$) in accordance with one embodiment of the present disclosure.

Given the array of NMR signal data ordered according to $q_s$ and $q_d$ coordinates. The two-dimensional plot is obtained by using a Laplace inversion and solving for $D_s$ and $D_d$ in equation 8. FIG. 16 shows a two-dimensional plot 1600 of diffusion coefficients at the first diffusion time ($D_s$) versus diffusion coefficients at the second diffusion time ($D_d$). For bulk diffusion, the diffusion coefficient is independent of the encoding time. Accordingly, the first diffusion coefficient ($D_s$) is equal to the second diffusion coefficient ($D_d$) and both are equal to the bulk diffusion coefficient ($D_0$). In this case, the NMR signal will appear on a diagonal line ("on-diagonal") 1602, as shown by component 1604 in FIG. 16. If the NMR signal or components of the NMR signal appear away from the diagonal line 1602 ("off-diagonal"), such as component 1606 in FIG. 16, then the first diffusion coefficient ($D_s$) and the second diffusion coefficient ($D_d$) are different. The off-diagonal components unambiguously identify the presence of restricted diffusion. Such variations in the time dependence of the apparent diffusion coefficient (D) is characteristic of restricted diffusion and will not occur due to fluid composition.

The off-diagonal components of the NMR signal can yield further information about the porous medium and fluid within the pore volumes of the porous medium. For example, the first coefficient ($D_s$) and the second diffusion coefficient ($D_d$) can be used to yield both pore size (e.g., a surface to volume ratio) and the bulk diffusion coefficient ($D_0$) of the fluid. The bulk diffusion coefficient (e.g., for fluid typing) and the pore size can be determined without knowing or assuming the specific fluid or pore size of the porous medium. For example, according to a short time diffusion approximation, restricted diffusion can be determined by the following relationship:

$$D_R(\Delta) \approx D_0 \left[ 1 - \left( \frac{4}{9\sqrt{\pi}} \right) \left( \frac{S}{V} \right) \sqrt{D_0 \Delta} \right] \quad (9)$$

where $D_R(\Delta)$ is the restricted diffusion over a time period $\Delta$, $D_0$ is the bulk diffusion coefficient, S is the surface area of the pores within the porous medium, and V is the volume of the pores within the porous medium. A short diffusion limit approximation can be applied in cases when addition information about the porous medium is not used (e.g., tortuosity or bulk diffusion coefficient). The short time diffusion approximation is derived in Mitra et al., Short-Time Behavior of the Diffusion Coefficient as a Geometrical Probe of Porous Media, Physical Review B, Vol. 47, No. 14, p. 8565-8574 (Apr. 1, 1993). The bulk diffusion coefficient can be determined according to the following relationship:

$$D_0 = \frac{\sqrt{2} D(\Delta) - D(2\Delta)}{\sqrt{2} - 1} \quad (10)$$

where $D(2\Delta)$ is the first diffusion coefficient ($D_s$) and $D(\Delta)$ is the combination ($\frac{1}{2}$)*($D_d$+Ds) of the second and first diffusion coefficient. The surface to volume ratio can be determined according to the following relationship:

$$\frac{S}{V} = \frac{9}{4} \sqrt{\frac{(\sqrt{2}-1)\pi}{\Delta}} \frac{D(\Delta) - D(2\Delta)}{(\sqrt{2} D(\Delta) - D(2\Delta))^{\frac{3}{2}}} \quad (11)$$

Various other formulations for the time dependent diffusion coefficient can also be applied to interpret the two-dimensional plot of diffusion at the first diffusion time ($D_s$) versus diffusion at the second diffusion time ($D_d$). For example, the Pade approximation can be used to incorporate a long time diffusion approximation of the diffusion coefficient, which includes the effects of tortuosity.

Various embodiments of the present disclosure are also directed to selecting appropriate pulse sequence parameters (e.g., diffusion time ($\Delta$ and $2\Delta$)) to accurately determine the bulk diffusion coefficient and surface-to-volume ratio. In some cases, the NMR signal may be on-diagonal (within a certain error) even though the nuclei within the pore volumes experience restricted diffusion. This condition may happen when the ratio of (i) the distance the nuclei diffuse to (ii) the pore size is small. Pore size scales as the reciprocal of the surface to volume ratio. The diffusion distance to pore size ratio is defined by a dimensionless number, referred to as $l_r$, and the following relationship:

$$l_r = (S/V)\sqrt{D_0 \Delta} \quad (12)$$

Equation 12 and the dimensionless number characterizes a range of pore sizes that can be accurately investigated using particular diffusion times ($\Delta$ and $2\Delta$). By using equation 12, appropriate diffusion times can be selected for a particular pore size and fluid type. Otherwise, in some cases, the diffusion distance of the nuclei will be too short to detect significant restricted diffusion in large pores (e.g., small $l_r$). In another case, for a closed pore network, the diffusion distance of the nuclei will be too long (e.g., large $l_r$) for a small pore size and diffusion attenuation will not be significantly different between $\Delta$ and $2\Delta$. In yet another example, for an open pore network, the diffusion distance of the nuclei will be too long (e.g., large $l_r$) for a small pore size and diffusion attenuation will approach a tortuosity limit (e.g., where $D(\Delta)$ does not significantly change).

To ensure that a desired range of restriction sizes is observable, numerical limits on the diffusion distance to pore size ratio ($l_r$) can be determined in order to evaluate sequence parameters ($\Delta$) for a given fluid type ($D_0$) and target restriction size. When pores are too large then $l_r$ is small (e.g., $l_r$ is less than 1) and the measurement will be limited by its ability to resolve small changes in the diffusion coefficient. The following relationship can be used to evaluate the change between the measured time dependent diffusion coefficients $D_d$ and $D_s$ at small $l_r$ by calculating a ratio between $D_d$ and $D_s$.

$$\frac{D_d}{D_s} = 2 \frac{1 - \kappa l_r}{1 - \sqrt{2\kappa l_r}} - 1, \kappa = \frac{4}{9\sqrt{\pi}}, \quad (13)$$

Thus, given a minimum desired contrast between $D_d$ and $D_s$, a lower bound for $l_r$ can be determined. For example, a 1% change between $D_s$ and $D_s$ (a ratio of 1/0.99) corresponds to a diffusion distance to pore size ratio ($l_r$) that is greater than 0.046.

An upper bound for the diffusion distance to pore size ratio ($l_r$) can also be estimated. For the upper bound, there are two cases to consider. In a first case, the sample includes a closed pore network (e.g., plant cells). In a second case, the sample includes, an open pore network (e.g., a rock core). For a closed pore network, at long diffusion times (Δ), the diffusion length will greatly exceed the pore size, but displacement of nuclei will be fixed by the pore size and, thus, the apparent diffusion coefficient will stop varying with diffusion time. An open pore network, at long diffusion times (Δ), will act as a free diffusion environment, but the apparent diffusion coefficient will be reduced from the true bulk value, as explained in Latour et al., Time-Dependent Diffusion Coefficient of Fluids in Porous Media as a Probe of Surface-to-Volume Ratio, Journal of Magnetic Resonance, Series A, Vol. 101, Issue 3, p. 342-346 (Feb. 15, 1993). Thus, the apparent diffusion coefficient for the open pore network will also stop varying with diffusion time. The diffusion distance to pore size ratio ($l_r$) is selected so that the ratio is sufficiently small to avoid a point where the apparent diffusion coefficient will stop varying with diffusion time. In some embodiments, the diffusion distance to pore size ratio ($l_r$) is selected to be less than five (e.g., $l_r<5$). For example, for sandstone rocks with large grains, the point where the apparent diffusion coefficient will stop varying with diffusion time is typically not reached because the NMR signal will decay before reaching large values of diffusion time (Δ). For carbonate rocks with fine grains, this point can be reached and thus the diffusion distance to pore size ratio ($l_r$) can be appropriately adjusted.

In various embodiments, the first set of pulses and the second set of pulses are pulsed field gradient pulses. For example, pulse sets 502 and 504 in FIG. 5 may be pulsed field gradient pulses. The pulsed field gradient pulses are applied to a substance using a gradient coil. In other embodiments, the pulse sets 502 and 504 can be radio frequency pulses that are applied to the substance using a constant field gradient produced by, for example, a permanent magnetic array. The radio frequency pulses in combination with the constant background gradient produce an "effective" pulsed field gradient within the substance. An effective pulsed field gradient has an equivalent effect on spin magnetization as a pulsed field gradient applied with a gradient coil.

Figure 17:
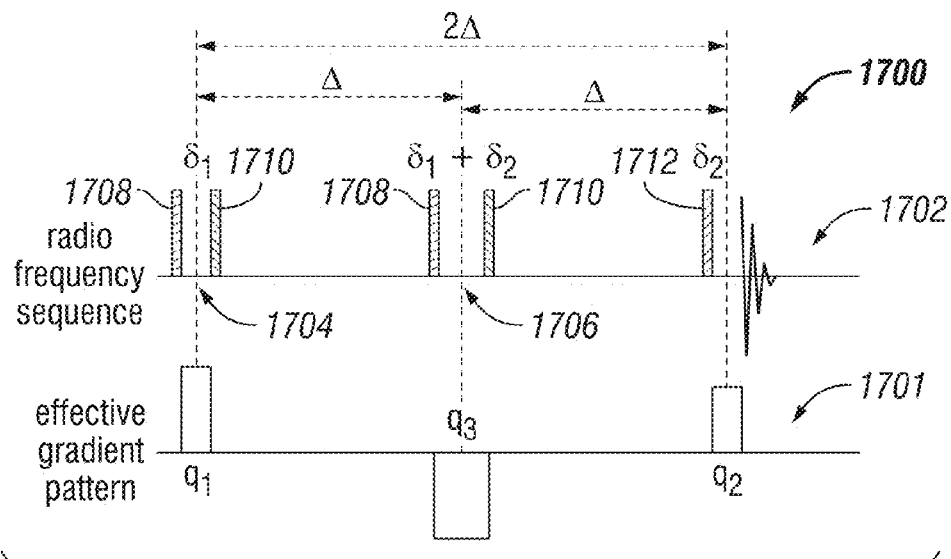
FIG. 17 shows an NMR pulse sequence that generates an effective pulsed field gradient using a constant background gradient in accordance with one embodiment of the present disclosure.

The effective pulsed field gradient can be produced by using pairs of pulses that encode the effective pulsed field gradient. FIG. 17 shows an NMR pulse sequence 1700 that generates an effective pulsed field gradient pattern 1701. The pulse sequence 1700 includes a series 1702 of 90-degree radio frequency pulses. The series 1702 includes a first pair of pulses 1704 and a second pair of pulses 1706. The first pulse 1708 within each pair rotates a spin magnetization of the nuclei to a transverse plane and begins gradient encoding. The second pulse 1710 in each pair rotates the spin magnetization back to a longitudinal axis and ends the gradient encoding. As shown in FIG. 17, the series of pulses 1702 effectively produce a corresponding effective gradient pattern 1701. The second 90-degree pulse in the last pair of pulses 1712 is omitted so that the NMR signal produced by the sequence 1700 can be detected. In the example shown in FIG. 17, the area parameters $q_1$ and $q_2$ are defined by the following relationships:

$$q_1 = \gamma g \delta_1, \quad (14)$$

$$q_2 = \gamma g \delta_2 \quad (15)$$

where $\delta_1$ and $\delta_2$ are the time periods between the pulses, as shown in FIG. 17. Accordingly, encoding for $q_s$ and $q_d$, as described above, can be accomplished by selecting $\delta_1$ and $\delta_2$ appropriately.

Figure 18:
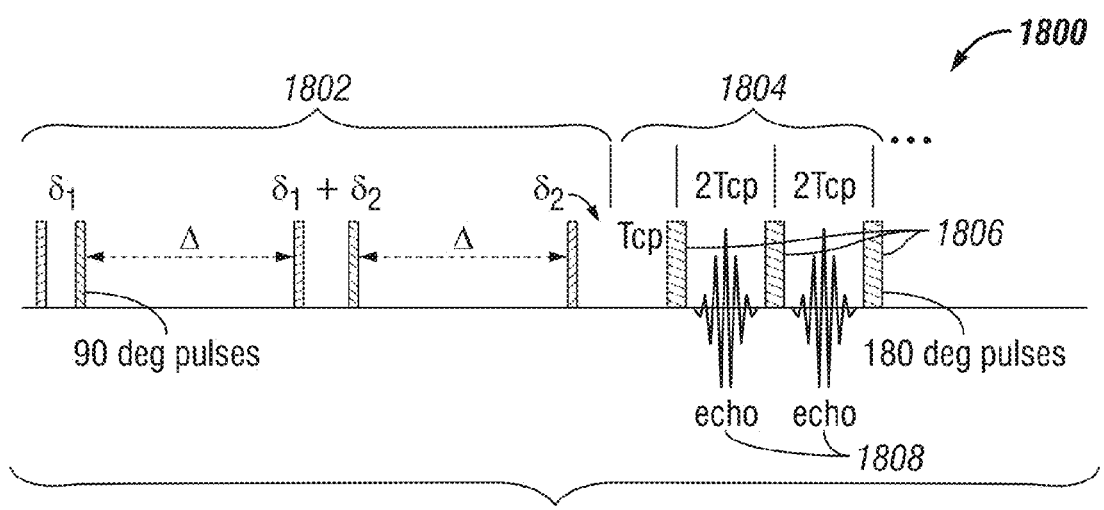
FIG. 18 shows an NMR pulse sequence that generates an effective pulsed field gradient in accordance with another embodiment of the present disclosure.

A number of refocusing pulses (e.g., 180-degree pulses) can follow the series of pulses and can be used to obtain $T_2$ relaxation time for the NMR signal. FIG. 18 shows a NMR pulse sequence 1800 with a series of pulses 1802 that generate an effective pulsed field gradient pattern followed by a CPMG sequence 1804. As shown in the FIG. 18, a 180-degree refocusing pulse 1806 is applied after each signal echo 1808 with a detection echo time of $2T_{cp}$. The CPMG sequence 1804 is used to record the signal decay, in a similar manner to $T_1-T_2$ and $D-T_2$ correlation techniques are applied. Such pulse sequences can be used in conjunction with NMR logging tools that employ permanent magnet arrays and produce field gradients that are constant in time.

Figure 19:
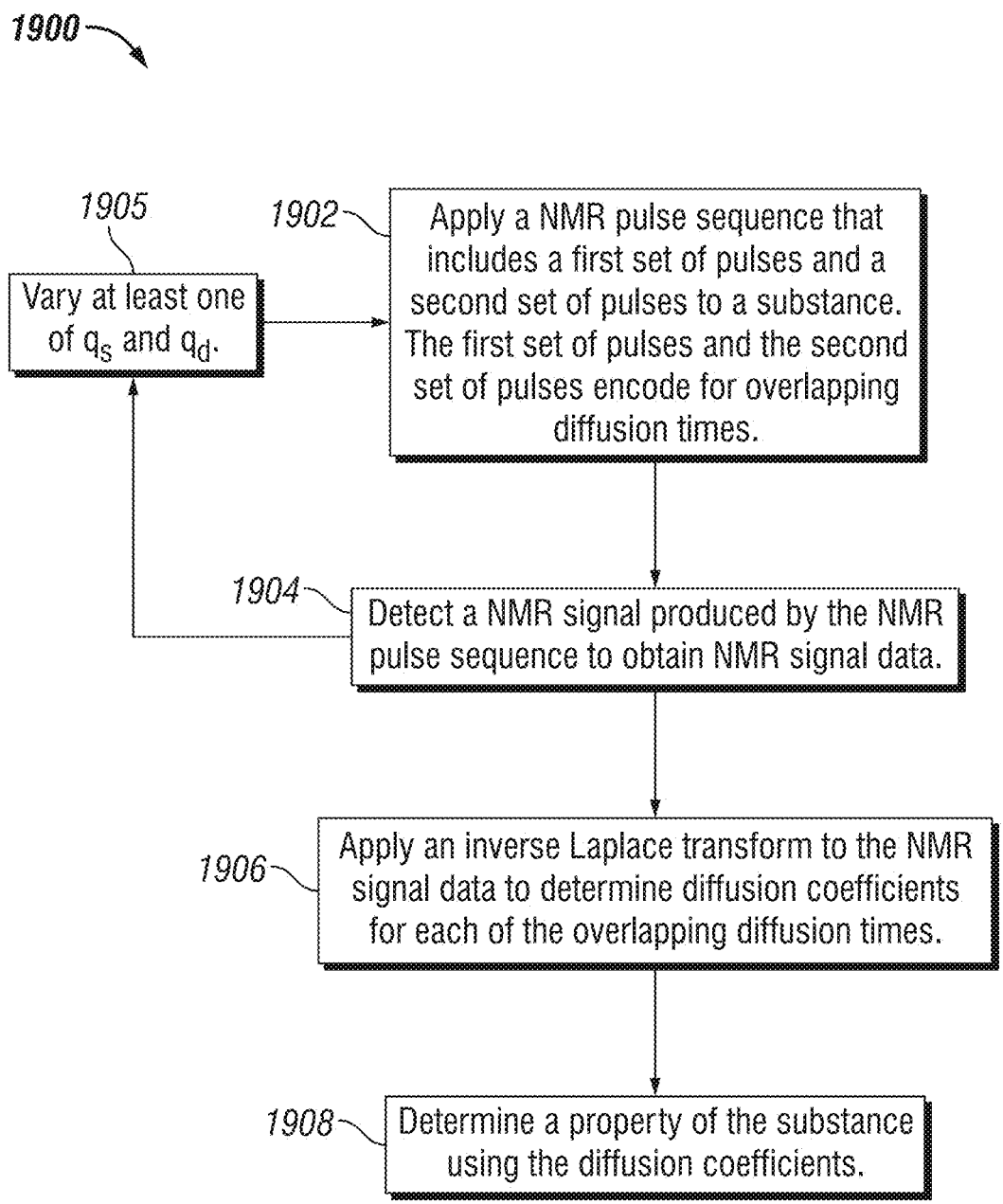
FIG. 19 shows a method for determining a property of a substance in accordance with another embodiment of the present disclosure.

FIG. 19 shows another method 1900 for determining a property of a substance using NMR. Before the first process 1902, a sample is placed in an NMR system. The sample may be a rock core, a food sample or a biological tissue. The NMR system may be a NMR rock core analyzer, a clinical or animal MRI, a portable NMR device, or a high field NMR spectrometer used in, for example, chemical spectroscopy. Process 1902 includes using the NMR system to apply a NMR pulse sequence to the substance. As explained above, the NMR pulse sequence includes at least a first set of pulses and a second set of pulses that encode for overlapping diffusion times. In particular, the NMR pulse sequence encodes for a first diffusion time (2Δ) and a second diffusion time (Δ), such as the pulse sequence 500 shown in FIG. 5. These sets of pulses include "portions" that have area parameters referred to herein as $q_s$ and $q_d$, as described above. The NMR signal data produced by the NMR pulse sequence is detected at process 1904.

Processes 1902 and 1904 are repeated a number of times (e.g., one or more times) using different values of $q_s$ and $q_d$ to obtain an array of NMR signal data ordered according to $q_s$ and $q_d$ coordinates (1905). The values of $q_s$ and $q_d$ can be varied independently. For example, for each value of $q_s$, several values of $q_d$ can be used. And vice versa, for each value of $q_d$, several values of $q_d$ can be used. The values for $q_s$ and $q_d$ may be uniformly spaced, logarithmically spaced, or have some other non-uniform spacing. Also, in some embodiments, $q_s$ and $q_d$ are aligned along the same spatial orientation if the orientation is not varied (e.g., the sample may be anisotropic). The measurement may then be repeated for other orientations. In another embodiment, a full sampling of $q_s$ and $q_d$ of magnitude and orientation space (e.g., forming a grid in x,y,(z)) may be used to obtain a map for the directionality of the first diffusion coefficient ($D_s$) versus the second diffusion coefficient ($D_d$). As an example, the directionality of each of these terms can be approximated by a tensor of a type that is similar to the type used in diffusion tenor imaging (DTI), which is common in the medical MRI field. Other pulse sequences can also be used. For example, an inversion recovery for $T_1$ relaxation time can be added before the first set and second set of pulses. In another example, a CPMG sequence for determining $T_2$ relaxation time or an MRI imaging sequence can be added after the first and second sets of pulses.

Figure 20:
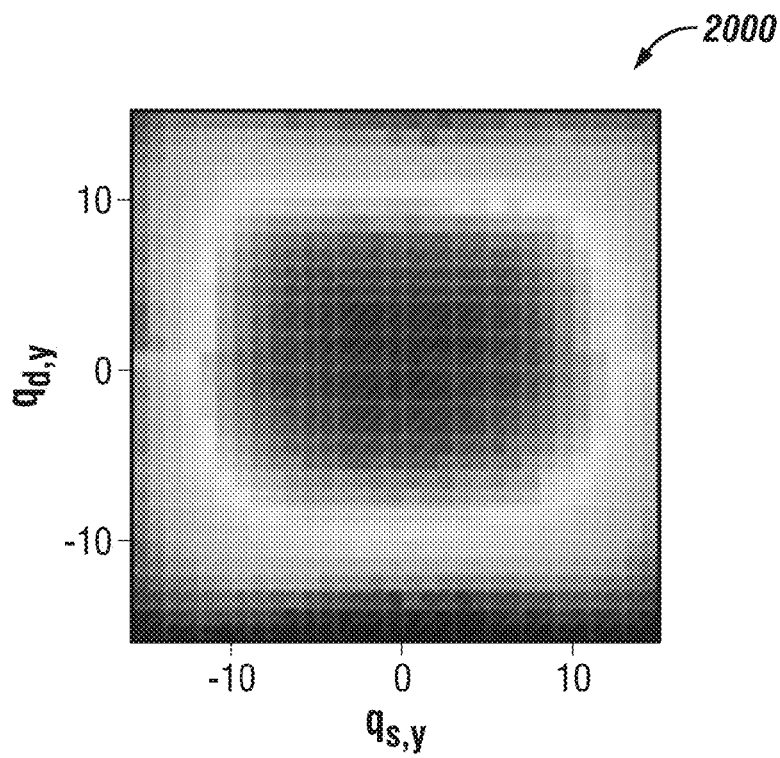
FIG. 20 shows an array of NMR signal data for a potato sample in accordance with one embodiment of the present disclosure.
Figure 21:
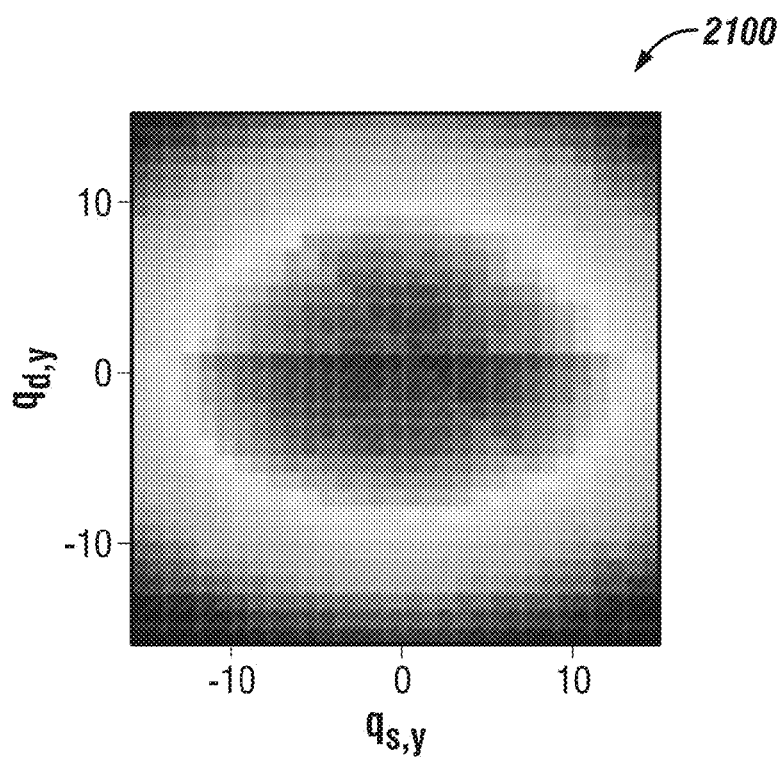
FIG. 21 shows an array of NMR signal data for an avocado sample in accordance with one embodiment of the present disclosure.

In various embodiments, the array of NMR signal data can be used to determine properties of the sample. For example, a faster decay along the $q_d$ axis than the $q_s$ axis indicates restricted diffusion. FIG. 20 shows an array of NMR signal data for a potato sample 2000. As shown in FIG. 20, the potato sample exhibits a faster decay along the $q_d$ axis than the $q_s$ axis. Furthermore, a non-ellipsoidal shape, as shown in FIG. 20, indicates a wide range of restriction sizes. In comparison, FIG. 21 shows an elliptical decay for an avocado sample 2100. Different pore sizes will produce different D(Δ)/D(2Δ) ratios and ellipsoids of varying eccentricity. In further embodiments, the array of NMR signal data is fit to a curve to determine effective D(Δ) to D(2Δ) scalar values for the sample by fitting a 2-dimensional Gaussian. If the orientations, in addition to the magnitudes, of $q_s$ and $q_d$ were varied, a full effective tensor approximation for D(Δ) and D(2Δ) can be determined by fitting a multi-dimensional Gaussian. In some embodiments, a fit up to the fourth order is made to include Kurtosis at the first diffusion time (2Δ) and the second diffusion time (Δ) in addition to Gaussian diffusion. Other decay shapes can also be used, such as a stretched exponential (e.g., $d_{\alpha,\beta}(t)=\exp\{-\alpha t^\beta\}$). Such decay shapes can be further tailored to fit $q_s$ and $q_d$. For example, given a one-dimensional stretched exponential $d_{\alpha,\beta}(|q|)$, a product $d_{s,\alpha,\beta}(|q_s|)\, d_{d,\alpha,\beta}(|q_d|)$ can be fit for $\alpha_s$, $\beta_s$, $\alpha_d$, $\beta_d$.

At process 1906, the method includes applying an inverse Laplace transform to the NMR signal data to obtain diffusion coefficients at each of the overlapping diffusion times. In particular, a two-dimensional inverse Laplace transform is applied to the array of NMR signal data along $q_s$ and $q_d$ to determine a two-dimensional plot of diffusion at the first diffusion time ($D_s$) versus diffusion at the second diffusion time ($D_d$), such as the one shown in FIG. 16. The two-dimensional inverse Laplace transform can be repeated for other spatial axis of $q_s$ and $q_d$ gradients. Furthermore, in some embodiments, additional encoding axes may also be inverted or fit. For example, with a CPMG acquisition, the $T_2$ relaxation time can be fit as a third dimension to an exponential decay or inverted for a third inverse Laplace dimension as a $T_2$ relaxation axis.

At process 1908, properties of the substance can be determined from the two-dimensional plot of diffusion coefficients at the first diffusion time ($D_s$) and diffusion coefficients at the second diffusion time ($D_d$). For example, the value of $D_s$ and $D_d$ (e.g., either a fit or a peak in the two-dimensional plot) can used to characterize both the fluid type (the bulk diffusivity $D_0$) and pore size (e.g., a surface-to-volume ratio) using relationships, such as those defined by equations 10 and 11. Furthermore, the two-dimensional plot can be analyzed to determine a distribution of bulk diffusivity $D_0$ and pore size. The signal from each plot element (e.g., at a particular $D_s$ and $D_d$ value) is projected onto a one-dimensional bulk diffusivity spectra ($D_0$) and onto a one-dimensional pore size spectra (e.g., surface-to-volume ratio). The diffusion time correlation plot may also be remapped for a two-dimensional plot of bulk diffusivity versus pore size. The diffusion time correlation plot can be used to separate out and identify different components of water and oil in different pore sizes. A diffusion time correlation plot could include additional dimensions, for example a $T_2$ coordinate for a $D_s$–$D_d$–$T_2$ plot.

The method described herein was performed on an avocado sample and a water sample. The avocado sample was cored from the edible portion (mesocarp) of a Haas avocado with a 2.5-mm inner diameter glass tube. This portion of the avocado includes cells averaging 60 μm in diameter, which contain 0.5 to 20 μm diameter oil droplets. The NMR signal of an avocado has multiple relaxation components corresponding to water and oil in different cellular environments. In this case, NMR signal data from water within vacuoles is used to analyze the avocado sample. The vacuole is the water storage compartment of a plant cell. Vacuolar water has the longest $T_2$ relaxation time (e.g., greater than 200 ms) of the other component fluids within the avocado. Thus, the NMR signal from other component fluids (e.g., oil) will have decayed away during the diffusion encoding time (e.g., 240 ms in total). As a fluid contained within a porous media, the vacuolar water signal should have components of both bulk diffusion and restricted diffusion.

An NMR pulse sequence, such as the one shown in FIG. 15, was applied to the avocado and water samples. The NMR pulse sequences included two sets of gradient pulses followed by a CPMG sequence. Additionally, a 180 degree refocusing pulse was spaced between the first pulse and second pulse within each set. The encoding parameters were: δ=4.0 ms, Δ=120 ms, and 2Δ=240 ms. The NMR pulse sequence was repetitively applied with various different value of $q_s$ and $q_d$. The values of $q_s$ and $q_d$ spanned between 0 and 82 cm$^{-1}$ for an 11-by-11 sampling array. The q values were calibrated based on the water sample assuming a bulk diffusion constant of 2.2×10$^{-5}$ cm$^2$/s.

Figure 22:
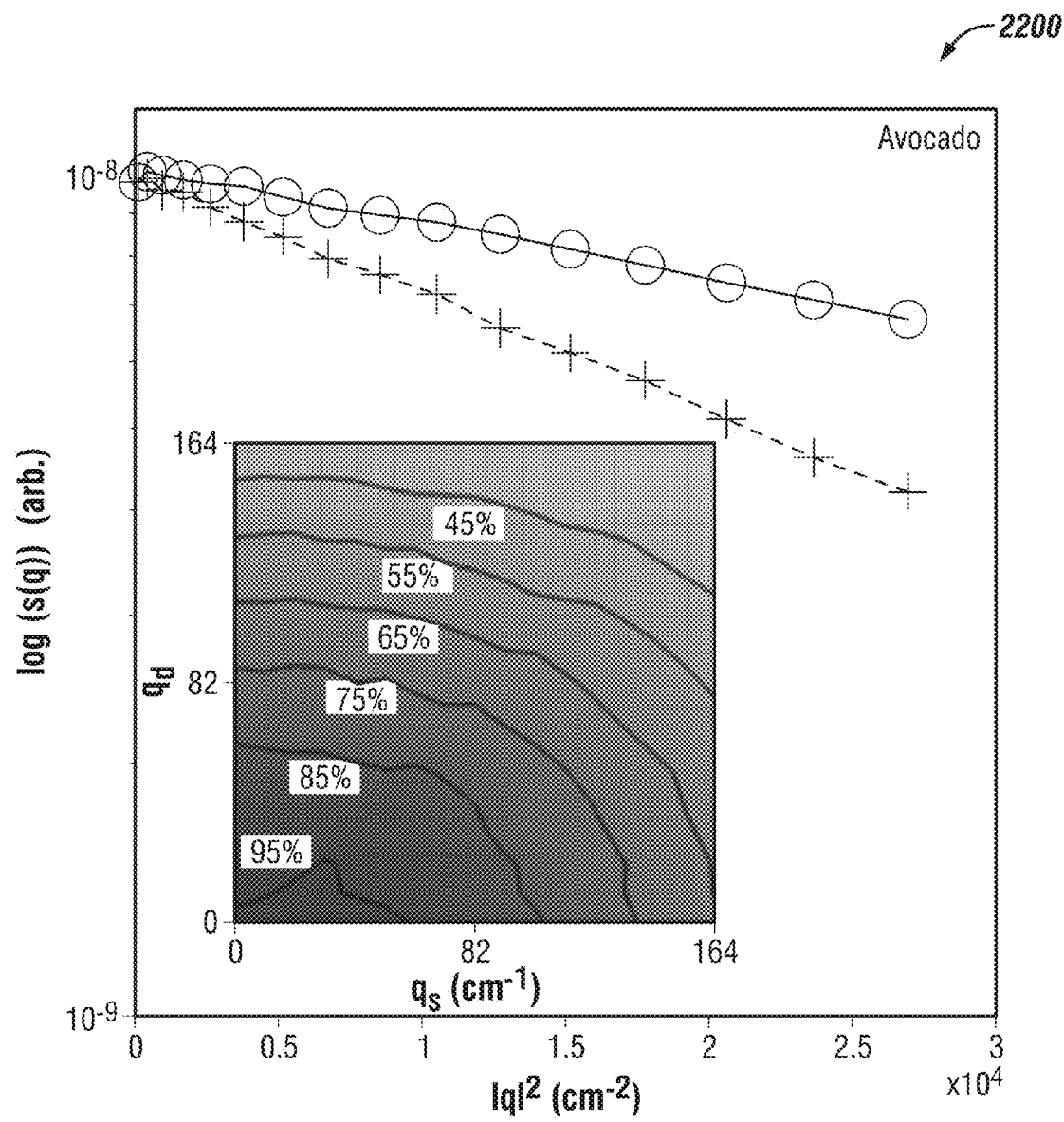
FIG. 22 shows NMR signal data as a function of $q_s$ and $q_d$ for an avocado sample in accordance with one embodiment of the present disclosure.
Figure 23:
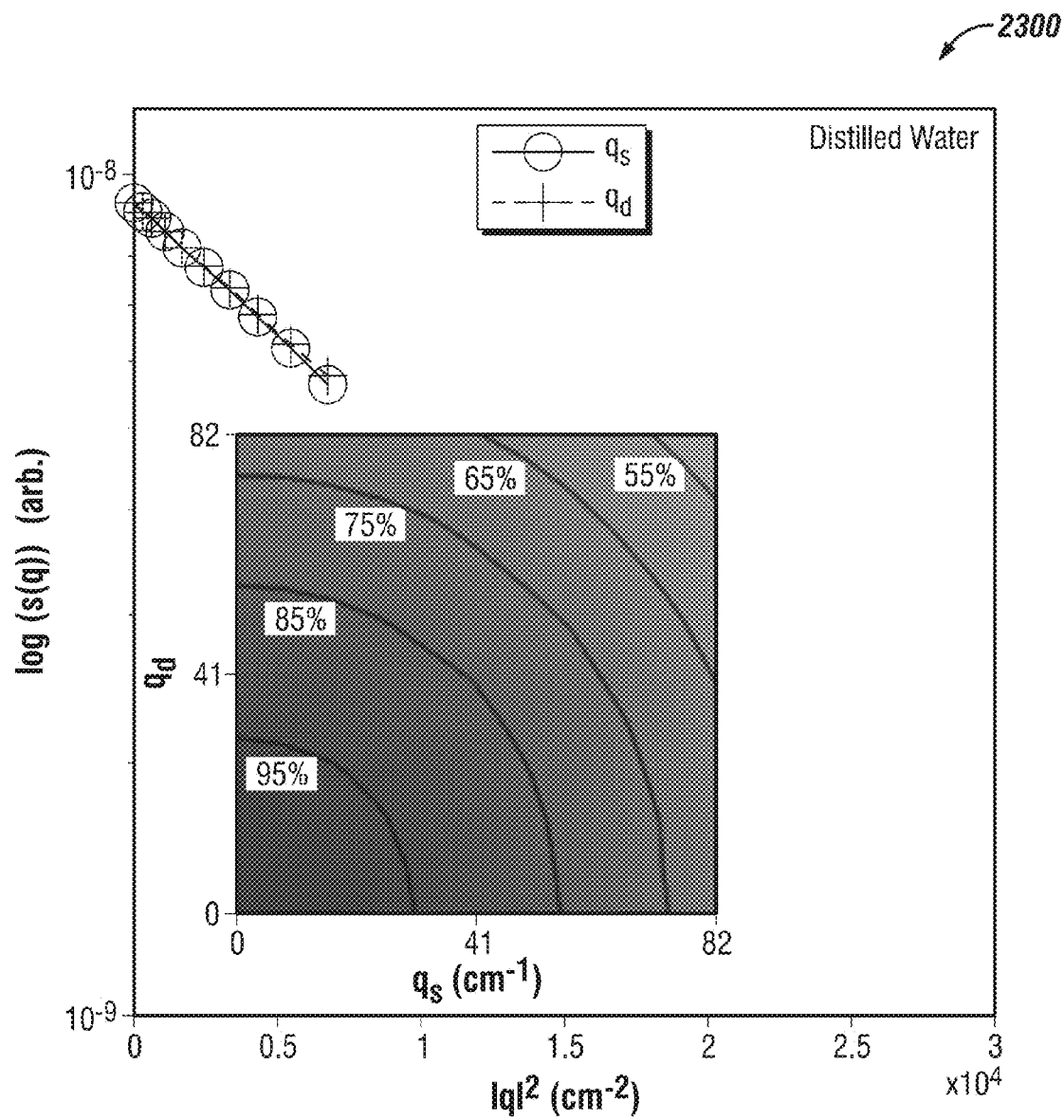
FIG. 23 shows NMR signal data as a function of $q_s$ and $q_d$ for a water sample in accordance with one embodiment of the present disclosure.

FIG. 22 shows the NMR signal data as a function of $q_s$ and $q_d$ for the avocado sample 2200, while FIG. 23 shows the NMR signal data as a function of $q_s$ and $q_d$ for the water sample 2300. For the water sample, the NMR signal data is radially symmetric in the $q_s$ and $q_d$ plane consistent with free diffusion and the absence of time-dependent diffusion. In contrast, the NMR signal shows a slower decay along the $q_s$ axis than along the $q_d$ axis. This indicates that the measured diffusion coefficient decreases with diffusion time, which indicates the presence of restricted diffusion. Furthermore, the pattern of the decay in the $q_s$ and $q_d$ plane shows that the principle axes are $q_s$ and $q_d$ confirming the form of equation 7. If these were not the principle axes, then the equation would not have this simple form and involve products of $q_s$ with $q_d$ (e.g., $q_s \times q_d$).

Figure 25:
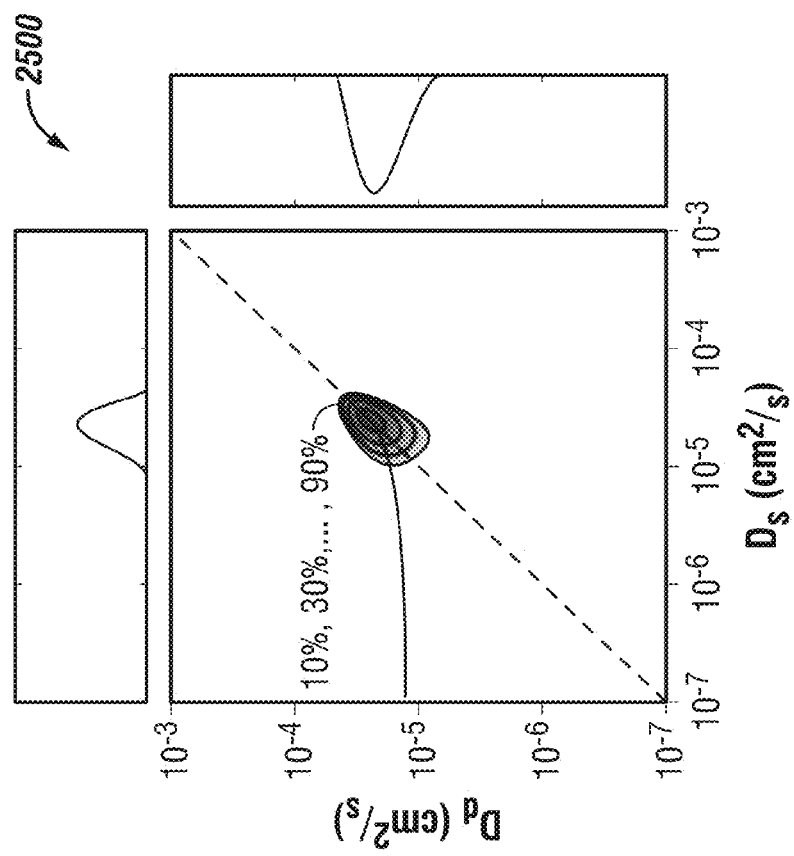
FIG. 25 shows a two-dimensional plot of diffusion coefficients for the water sample in accordance with one embodiment of the present disclosure.
Figure 24:
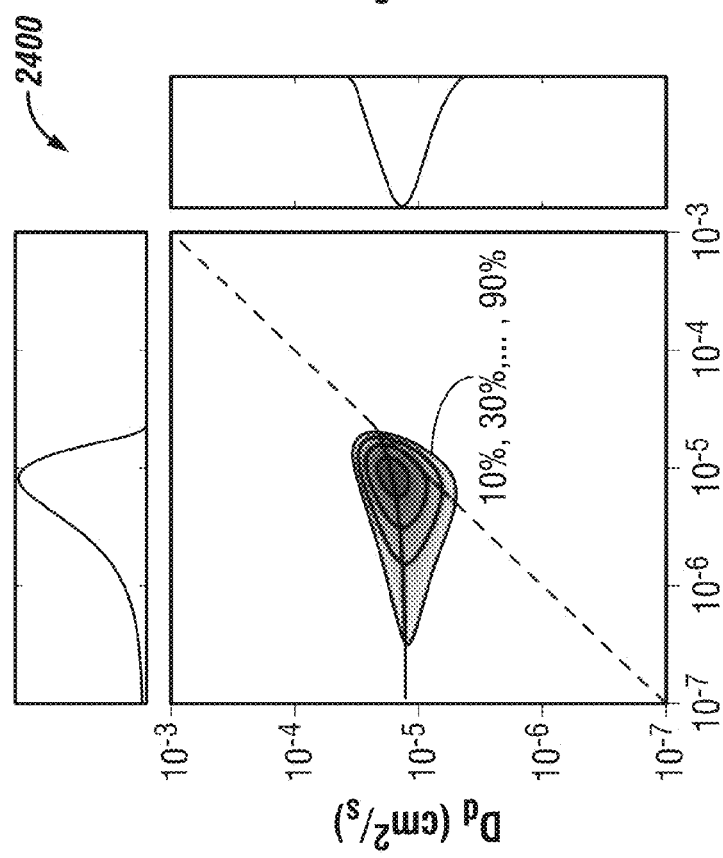
FIG. 24 shows a two-dimensional plot of diffusion coefficients for the avocado sample in accordance with one embodiment of the present disclosure.

A two-dimensional Laplace inversion was applied to the NMR signal data from the avocado sample and the water sample to produce a two-dimensional plot of diffusion at a first diffusion time ($D_s$) and diffusion at a second diffusion time ($D_d$). FIG. 24 shows the two-dimensional plot of diffusion coefficients for the avocado sample 2400, while FIG. 25 shows the two-dimensional plot of diffusion coefficients for the water sample 2500. FIG. 24 shows off-diagonal components for the avocado sample and FIG. 25 shows that the NMR signal is on-diagonal for the water sample. These results are consistent with restricted and free diffusion for the respective samples. Furthermore, the NMR signal data directly overlays with a curved line corresponding to a restricted diffusion model for water, as defined by equation 9.

The linear mean values of $D_s$ and $D_d$ are (2.2; 2.2) and (0.63; 1.45)×10$^{-5}$ cm$^2$/s for the water sample and avocado sample, respectively. Applying equations 10 and 11 to the NMR signal data a value of 2.02×10$^{-5}$ cm$^2$/s for the bulk diffusion coefficient ($D_0$) of vacuolar water and a value of 554 cm$^{-1}$ (or a 108 μm spherical diameter) for the pores within the avocado sample are obtained. This diameter is slightly larger than the nominal size of the typical vacuoles of an avocado fruit. This overestimate happens for three reasons. Firstly, the diffusion length of the nuclei was 31 μm (e.g., diffusion length=$\sqrt{2D_0(2\Delta)}$), which is a significant fraction of the pore size (e.g., small $l_r$). The diffusion time could be decreased to determine a better approximation of the pore size. Secondly, plant cells are rectangular in nature and diffusion is fully constrained within this compartment. Thus the measured surface-to-volume ratio should correspond to a smaller length than that of a spherical cell. Overall, the properties obtained for the avocado and water sample agreed with the cellular geometry in an avocado fruit.

Figure 26:
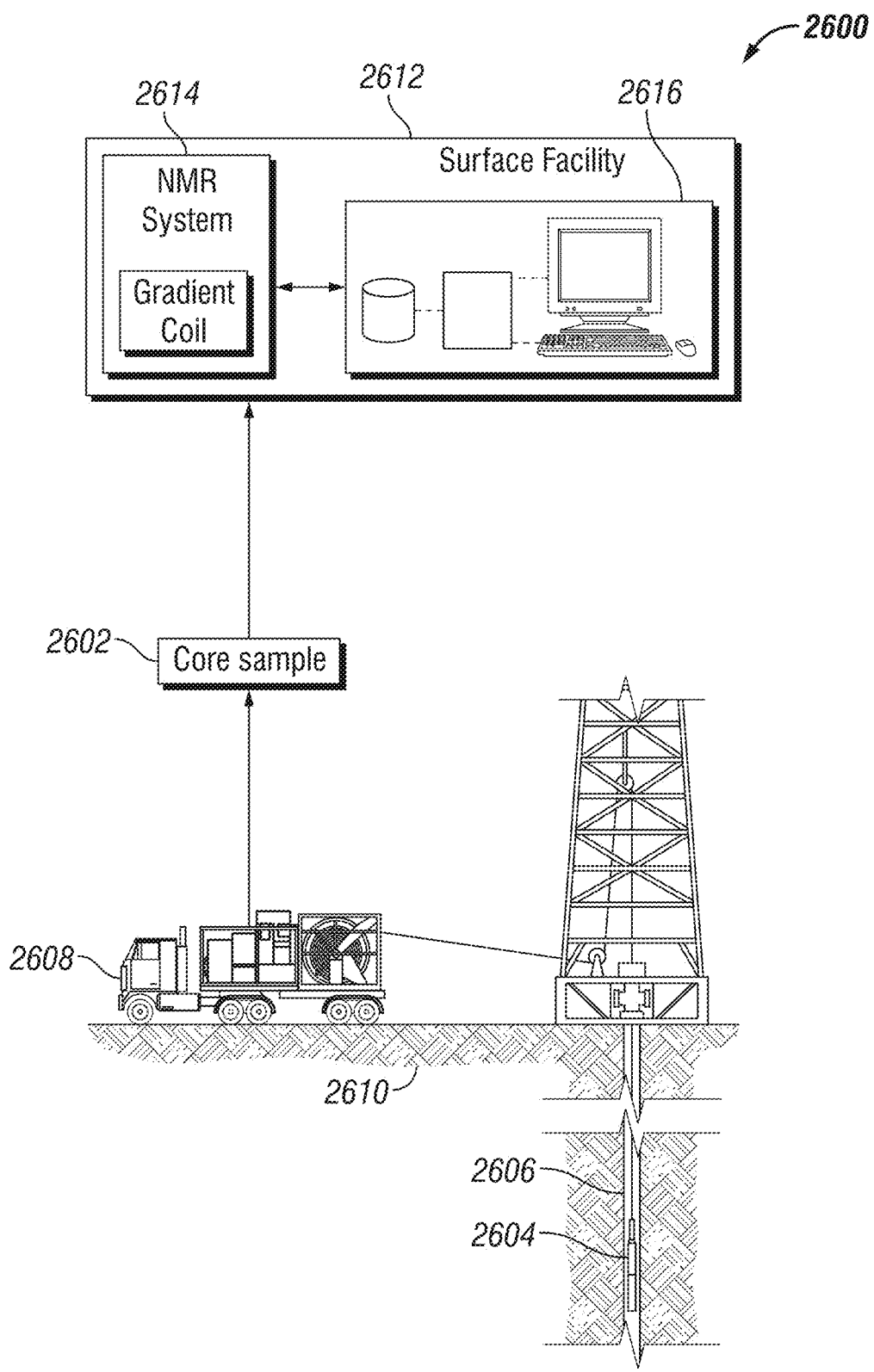
FIG. 26 shows a rock core system for determining properties of a rock core sample in accordance with one embodiment of the present disclosure.

FIG. 26 shows a rock core system 2600 for determining properties of a rock core sample 2602. The system 2600 includes a wireline tool string 2604 that is deployed in a well 2606 via a wireline truck 2608. The wireline tool 2604 is a downhole tool adapted to remove the core sample 2602 from a formation 2610. Once the core sample 2602 is obtained, the core is transported to a surface facility 2612, which includes an NMR system 2614 and operator module 2616 for carrying out the methods and processes described herein, as well as other processing. According to some embodiments, the surface facility 2612 may be located in a location remote from the well 2606.

The operator module 2616 includes a computer system (e.g., a processor and a memory) that supports a graphical user interface (GUI), such as a monitor, a touch screen, a mouse, a keyboard and/or a joystick. The GUI allows an operator to control and communicate with the NMR system 2614. The NMR system 2614 may include a gradient element 2618 for applying pulsed field gradient pulses to the core sample 2602 (e.g., a gradient insert). In various embodiments, the gradient element 2618 is a metal wound coil. The NMR system 2614 includes a corresponding electrical power supply to inject electrical current into the coil. The gradient coil may be designed with a particular geometry so that the magnetic field produced by the coil spatially varies over the sample. The spatial variation may be designed to have a constant gradient along a particular direction. This direction is referred to herein as "a gradient direction." In illustrative embodiments, three sets of such gradient coils are provided along three gradient directions (e.g., the Cartesian coordinates—x, y, and z) in order to provide imaging in three dimensions, such as in a medical MRI application. Other NMR systems may be equipped with one or two such gradient coil sets so that spatial resolution can be achieved along 1 or 2 directions.

In one specific embodiment, the rock core system 2600 is used to analyze a water flooded rock core sample (e.g., initially oil saturated) 2602. The rock core sample 2602 is removed from the formation 2610 using the wireline tool 2604. The rock core sample 2602 is placed into the NMR system 2614. In this case, the NMR system 2614 includes a single z-axis gradient coil. A pulse sequence is applied to the rock core sample 2602 using the NMR system 2614. The pulse sequence includes two sets of gradient pulses followed by a CPMG acquisition to encode for $T_2$ relaxation time. The sequence is repeated and $q_{sz}$ and $q_{dz}$ are incremented over a two-dimensional $q_s$ and $q_d$ Cartesian array for each acquisition to obtain NMR signal data. A three-dimensional inverse Laplace transform is performed to convert the NMR data into a three-dimensional plot of $D_s$, $D_d$, and $T_2$ relaxation time. Peaks are identified within the three-dimensional plot (e.g., water, oil). In the case of light oils, water in small pores with a similar apparent diffusion coefficient and $T_2$ to the oil are now separated in the $D_s$ and $D_d$ plane. In some embodiments, the $D_s$ and $D_d$ plot can be converted into a bulk diffusion coefficient ($D_0$) and surface-to-volume ratio (S/V) plot by converting each $D_s$ and $D_d$ coordinate into $D_0$ and S/V coordinates via equations 10 and 11. As explained above, the equations use the short time diffusion approximation. Other alternative equations can also be used. Fluid type and pore size of the rock core sample 2602 may then be identified based on NMR signal position on these axes. The $T_2$ relaxation time may then identify spines in pores too small or large to be characterized by the $D_s$ and $D_d$ measurement.

In another example, the rock core system 2600 is used to analyze a cleaned brine saturated rock core sample 2602. The rock core sample 2602 is analyzed to determine a three-dimensional plot of $D_s$, $D_d$, and $T_2$ relaxation time. The $D_s$ and $D_s$ axes can be converted into bulk diffusion coefficient ($D_0$) and surface-to-volume ratio (S/V) axes using equations 10 and 11, as explained above. This plot relates the values of the surface-to-volume ratio to respective values of $T_2$ relaxation time. The surface-to-volume ratio and the $T_2$ relaxation time values are related a surface relaxivity of the pores according to the following relationship.

$$\frac{1}{T_2} = \frac{1}{T_{2,bulk}} + \rho \frac{S}{V} \qquad (16)$$

where $T_2$ is the measured $T_2$ relaxation time, $T_{2,bulk}$ is the $T_2$ relaxation time for the fluid in a bulk environment, and $\rho$ is the surface relaxivity of the pores. The relationship between the surface-volume-ratio and the $T_2$ relaxation time can be determined by plotting the two values. A relationship that varies indicates that pores of different sizes have different pore surface properties.

Figure 27:
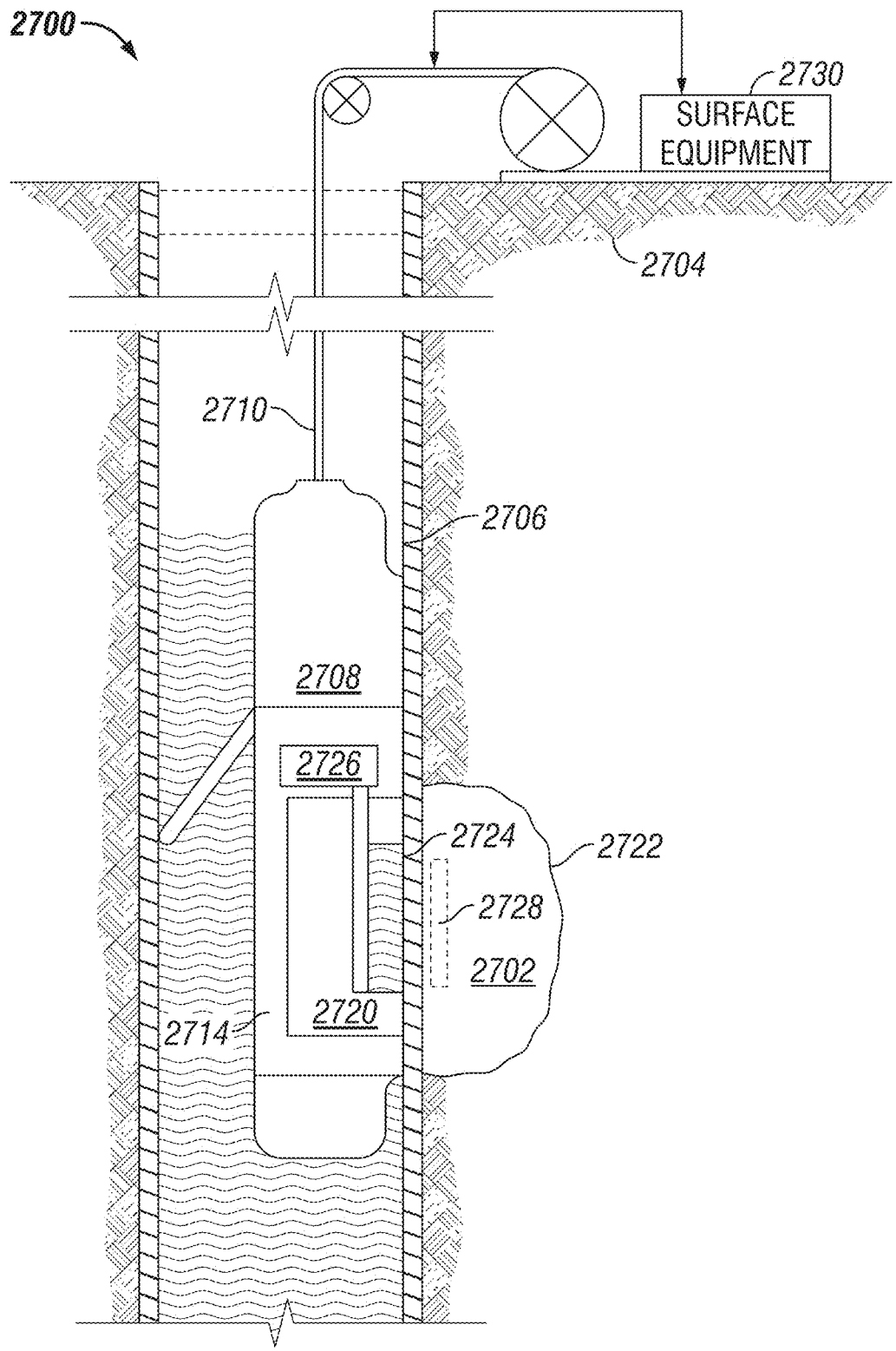
FIG. 27 shows a wireline system for determining properties of an earth formation in accordance with one embodiment of the present disclosure.

FIG. 27 shows a wireline system 2700 for determining properties of an earth formation. The wireline system 2700 is used to investigate, in situ, a substance 2702 within the earth formation 2704 surrounding a wellbore 2706 to determine a property of the substance. As shown in FIG. 27, a wireline tool 2708 is disposed within the wellbore 2706 and suspended on an armored cable 2710. Although the wireline tool 2708 is shown as a single body in FIG. 27, the tool may alternatively include separate bodies. As shown in FIG. 27, the wireline tool 2708 includes an NMR logging module 2714 that is used to apply NMR pulse sequences to the formation 2704. The NMR logging module 2714 includes an electro-magnetic device 2720 for applying a static magnetic field to a sensitivity zone 2722 within the earth formation 2704. In some embodiments, the electro-magnetic device 2720 is a magnet or an array of magnets formed from a magnetic material. The NMR logging module 2714 also includes at least one coil 2724 and NMR electronics 2726 electronically coupled to the coil. The coil 2724 and NMR electronics 2726 apply an oscillating field to an area of interest 2728 within the earth formation 2704. The area of interest 2702 is located within the sensitivity zone 2722 of the electro-magnetic device 2720. In accordance with various embodiments of the present disclosure, the oscillating field applied to the earth formation 2704 includes the NMR pulse sequences described above. In various embodiments, the wireline tool 2708 does not include a gradient coil. In such embodiments, an effective pulsed field gradient is produced by the two sets of pulses. FIG. 18 shows an example of an NMR pulse sequence that produces an effective pulsed field gradient. The NMR pulse sequences are repeated for a selected range of $q_s$ and $q_d$ by choosing corresponding values of $\delta_1$ and $\delta_2$, as described with respect to FIGS. 17 and 18. The NMR signal data produced by the sequences is detected using the coil 2724 and used to analyze the formation using the methods and processes described above. The wireline system 2700 also includes surface equipment 2730 for supporting the wireline tool 2708 within the wellbore 2706. In various embodiments, the surface equipment 2730 includes an operator interface for communicating with the NMR logging module 2714. Such an operator interface has already been described with reference to FIG. 26. In some embodiments, the NMR logging module 2714 and operator module communicate through the armored cable 2710.

The NMR systems and methods described herein are not limited to any device type or system. The NMR systems and methods described herein can be implemented in surface environments, such as a laboratory. The systems and methods described herein are also not limited to application in any type of particular field. For example, the systems and methods can be used to analyze biological tissues, such as bone tissue or brain tissue. Many biological tissues include porous media and characterization of the microstructure, the pore sizes, and the intrinsic diffusion coefficient of tissues is useful in the field of clinical medicine. The systems and methods described herein can be applied to the study such tissue structure and can be combined with MRI for clinical use.

With respect to wellbore applications, the NMR systems and methods described herein are not limited to wireline systems, such as the one shown in FIG. 27. For example, illustrative embodiments can also be used with any suitable means of conveyance, such coiled tubing. Various embodiments of the present disclosure may also be applied in logging-while-drilling (LWD) systems (e.g., a LWD tool) or measuring-while-drilling systems (e.g., MWD tools).

The processes described herein, such as (1) applying NMR pulse sequences to a substance, (2) acquiring an array of NMR signal data for $q_s$ and $q_d$ values, (3) determining properties of the substance using the array of NMR signal data, (4) performing an inverse Laplace transform on the array of NMR signal data to determine a plot diffusion coefficients, (5) identifying peaks within the plot, (6) determining a bulk diffusion coefficient of the substance using the plot, and (7) determining a surface-to-volume ratio of the substance using the plot, can be performed and implemented at least in part by a computer system.

The term "computer system" should not be construed to limit the embodiments disclosed herein to any particular device type or system. The computer system may be a laptop computer, a desktop computer, or a mainframe computer. The computer system may also include a computer processor (e.g., a microprocessor, microcontroller, digital signal processor or general purpose computer) for executing any of the methods and processes described above (e.g., processes (1)-(7)). The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. This memory may be used to store, for example, the NMR pulse sequences and acquired NMR signal data, as described above.

Any of the methods and processes described above, including processes (1)-(7) as listed above, can be implemented as computer program logic for use with the computer processor. The computer program logic may be embodied in various forms, including a source code form or a computer executable form. Source code may include a series of computer program instructions in a variety of programming languages (e.g., an object code, an assembly language or a high-level language such as C, C++ or JAVA). Such computer instructions can be stored in a non-transitory computer readable medium (e.g., memory) and executed by the computer processor. For example, the NMR pulse sequences described herein may be implemented as a series of computer instructions that define the characteristics of at least some of the NMR pulse sequences described herein (e.g., pulse amplitude, pulse phase, pulse duration, first area parameter, second area parameter, and diffusion times (Δ and 2Δ)). The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

The invention claimed is:

1. A method for determining a property of a substance using nuclear magnetic resonance (NMR), the method comprising:
    applying a NMR pulse sequence comprising a first set of pulses and a second set of pulses to the substance, wherein the first set of pulses and the second set of pulses encode for overlapping diffusion times;
    detecting a NMR signal produced by the NMR pulse sequence to obtain NMR signal data; and
    determining the property of the substance using the NMR signal data over each of the overlapping diffusion times
    (i) the first set of pulses comprises two pulses that are each defined by a first area parameter and separated by a time period, and
    (ii) the second set of pulses comprises two pulses that are each defined by a second area parameter and separated by the time period;
    applying the NMR pulse sequence to the substance a plurality of times using different values for the first area parameter and the second area parameter;
    detecting NMR signals produced by the NMR pulse sequence for the different values of the first area parameter and the second area parameter to obtain NMR signal data.

2. The method of claim 1, wherein
    (i) the overlapping diffusion times comprise a first diffusion time and a second diffusion time, and
    (ii) the first set of pulses and the second set of pulses comprise a portion of pulses that correspond to the first diffusion time and a complimentary portion of pulses that correspond to the second diffusion time.

3. The method of claim 2, wherein the values of the first area parameter and the second area parameter are varied according to the following relationships:

$$q_s = q_1 + q_2,$$

$$q_d = q_2 - q_1,$$

where $q_1$ is the first area parameter, $q_2$ is the second area parameter, $q_s$ is an area parameter for the portion of pulses that correspond to the first diffusion time, and $q_d$ is an area parameter for the complimentary portion of pulses that correspond to the second diffusion time.

4. The method of claim 3, further comprising:
    performing a Laplace inversion on the NMR signal data to obtain diffusion coefficients for the first diffusion time and the second diffusion time.

5. The method of claim 1, wherein the substance is a porous medium containing a fluid.

6. The method of claim 5, wherein the substance is a rock core containing oil, water, or both.

7. The method of claim 6, further comprising:
removing the rock core from a formation.

8. The method of claim 5, wherein the property is (i) a bulk diffusion coefficient for the fluid, (ii) a surface-to-volume ratio for the porous medium, or (iii) both.

9. The method of claim 1, wherein the first set of pulses and the second set of pulses comprise pulsed field gradient pulses.

10. The method of claim 9, wherein the pulsed field gradient pulses are applied to the substance using a gradient coil.

11. The method of claim 1, wherein a constant field gradient is applied to the substance and the first set of pulses and the second set of pulses are radio frequency pulses that produce an effective pulsed field gradient within the substance.

12. The method of claim 1, wherein
(i) the two pulses within the first set of pulses include pulse areas that cancel, and
(ii) the two pulses within the second set of pulses include pulse areas that cancel.

13. The method of claim 1, wherein a time period between the first set of pulses and the second set of pulses is less than the two overlapping diffusion times.

14. A method for determining a property of a substance using nuclear magnetic resonance (NMR), the method comprising:
applying a NMR pulse sequence comprising a first set of pulses and a second set of pulses to the substance, wherein the first set of pulses and the second set of pulses encode for overlapping diffusion times;
detecting a NMR signal produced by the NMR pulse sequence to obtain NMR signal data; and
determining the property of the substance using the NMR signal data over each of the overlapping diffusion times wherein the substance is a fluid within an underground formation and the NMR sequence is applied to the fluid using a NMR logging tool.

15. A method for determining a property of a substance using nuclear magnetic resonance (NMR), the method comprising:
applying an NMR pulse sequence to the substance, wherein (i) the NMR pulse sequence comprises a first set of pulses and a second set of pulses, (ii) the first set of pulses and the second set of pulses encode for a first diffusion time and a second diffusion time, (iii) the first diffusion time and a second diffusion time overlap, (iv) the first set of pulses comprises two pulses that are each defined by a first area parameter and separated by a time period, and (v) the second set of pulses comprises two pulses that are each defined by a second area parameter and separated by the time period;
detecting a NMR signal produced by the NMR pulse sequence to obtain NMR signal data;
applying the NMR pulse sequence and detecting the NMR signal produced by the NMR pulse sequence a number of times using different values for at least one of the first area parameter and the second area parameter;
performing a Laplace inversion on the NMR signal data to obtain diffusion coefficients for the first diffusion time and the second diffusion time; and
determining the property of the substance using the diffusion coefficients.

16. The method of claim 15, wherein the property is a bulk diffusion coefficient, a surface-to-volume ratio, or both.

17. The method of claim 15, wherein the first set of pulses and the second set of pulses comprise a portion of pulses that correspond to the first diffusion time and a complimentary portion of pulses that correspond to the second diffusion time.

18. The method of claim 17, wherein the values of the first area parameter and the second area parameter are varied according to the following relationships:

$$q_s = q_1 + q_2,$$

$$q_d = q_2 - q_1,$$

where $q_1$ is the first area parameter, $q_2$ is the second area parameter, $q_s$ is an area parameter for the portion of pulses that correspond to the first diffusion time, and $q_d$ is an area parameter for the complimentary portion of pulses that correspond to the second diffusion time.

19. The method of claim 15, wherein a time period between the first set of pulses and the second set of pulses is less than the first diffusion time and the second diffusion time.

* * * * *